(12) United States Patent
Martin et al.

(10) Patent No.: US 8,388,972 B2
(45) Date of Patent: Mar. 5, 2013

(54) HUMAN ANTI-FOLATE RECEPTOR ALPHA ANTIBODIES AND ANTIBODY FRAGMENTS FOR THE RADIOIMMUNOTHERAPY OF OVARIAN CARCINOMA

(75) Inventors: Franck Martin, L'Aquila (IT); Margherita Cattozzo, L'Aquila (IT); Giovanni Maurizi, L'Aquila (IT); Vito Di Cioccio, L'Aquila (IT); Mariangela Figini, Milan (IT); Silvana Canevari, Milan (IT)

(73) Assignees: Advanced Accelerator Applications S.A., Saint Genis Pouilly (FR); Istituto Nazionale per Lo Studio E la Cura Dei Tumori, Milan (IT)

( * ) Notice: Subject to any disclaimer, the term of this patent is extended or adjusted under 35 U.S.C. 154(b) by 232 days.

(21) Appl. No.: 12/441,207

(22) PCT Filed: Sep. 12, 2007

(86) PCT No.: PCT/EP2007/007944
§ 371 (c)(1),
(2), (4) Date: May 13, 2009

(87) PCT Pub. No.: WO2008/031577
PCT Pub. Date: Mar. 20, 2008

(65) Prior Publication Data
US 2010/0055034 A1   Mar. 4, 2010

(30) Foreign Application Priority Data
Sep. 15, 2006   (EP) .................................... 06019399

(51) Int. Cl.
*A61K 39/395* (2006.01)
*A61K 51/10* (2006.01)
*C07K 16/00* (2006.01)
*C07H 21/04* (2006.01)
*C12N 1/21* (2006.01)
*G01N 33/53* (2006.01)

(52) U.S. Cl. ............. 424/178.1; 530/388.22; 530/389.1; 530/391.3

(58) Field of Classification Search ................ 424/178.1; 530/388.2, 389.1, 391.3
See application file for complete search history.

(56) References Cited

U.S. PATENT DOCUMENTS
2010/0216190 A1   8/2010   Martin et al.

FOREIGN PATENT DOCUMENTS
| EP | 05109274.0 | 10/2005 |
| WO | WO 03/074679 | 9/2003 |
| WO | WO 2004/003019 | * 6/2004 |
| WO | WO 2007/039632 | 4/2007 |

OTHER PUBLICATIONS

Figini et al. (Can. Immunol. Immunother. 58:531-546 (Aug. 15, 2008)).*
Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Girshick, "The Kappa Gene Repertoire of Human Tonsil B. Cells," accession No. AAQ21828, Department of Pediatrics, Section of Pediatric Rheumatology, University of Wuerzburg, Jun. 11, 2003.
Coliva et al., "Y Labeling of Monoclonal Antibody M0v18 and Preclinical Validation for Radioimmunology of HIman Ovarian Carcinomas," Cancer Immunol. Immunother, 2005, 54(12):1200-1213.
Figini et al., "Panning Phage Antibody Libraries on Cells: Isolation of Human Fab Fragments Against Ovarian Carcinoma Using Guided Selection," Cancer Research, Mar. 1, 1998, 58(5):991-996.
Melani et al., "Targeting of Interleukin 2 to Human Ovarian Carcinoma by Fusion with a Single-Chain Fv of Antifolate Receptor Antibody," Cancer Research, Sep. 15, 1998, 58(18):4146-4154.
International Search Report dated Nov. 30, 2007 corresponding to PCT/EP2007/007944.
Jemal, A. et al. Cancer statistics, *CA Cancer J. Clin.* 2005, vol. 55, pp. 10-30.
Cannistra, S.A. Cancer of the ovary, *N. Engl. J. Med.* 2004, vol. 351, pp. 2519-2529.
Matulonis, U. et al., Cancer of the Ovary, N. Engl. J. Med., Mar. 24, 2005, vol. 352, Issue 12.
Harries, M. et al. Part I: chemotherapy for epithelial ovarian cancer-treatment at first diagnosis. Lancet Oncol. 2002, vol. 3 pp. 529-536.
Vasey P.A. Resistance to chemotherapy in advanced ovarian cancer: mechanisms and current strategies, *Br. J. Cancer*, 2003, 89 Suppl., vol. 3, pp. S23-S28.
Bast, R.C. et al. A radioimmunoassay using a monoclonal antibody to monitor the course of epithelial ovarian cancer, *N. Engl. J. Med.* Oct. 13, 1983, vol. 309, Issue 15, pp. 883-887.

(Continued)

*Primary Examiner* — Lynn Bristol
(74) *Attorney, Agent, or Firm* — Steinfl & Bruno, LLP

(57) ABSTRACT

Antibody or fragment thereof, which specifically binds to folate receptor-alpha (FRα), wherein said antibody or fragment thereof comprises a light chain whose variable region comprises at least one of the following amino acid sequences: —RASESVSFLGINLIH (SEQ ID NO: 3), —QASNKDT (SEQ ID NO: 4), —LQSKNFPPYT (SEQ ID NO: 5), and wherein the constant region of said light chain is a kappa constant region.

15 Claims, 13 Drawing Sheets

OTHER PUBLICATIONS

Figure 2:
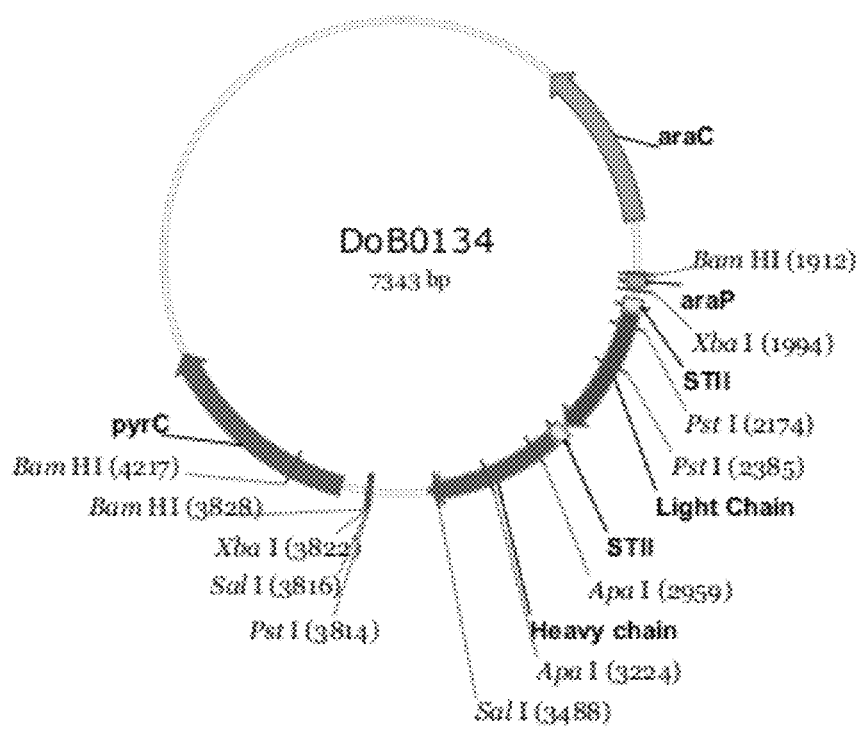

Lavin, P.T. et al. CA 125 for the monitoring of ovarian carcinoma during primary therapy, *Obstet Gynecol.* Feb. 1987, vol. 69, Issue 2, pp. 223-227.

Miotti, S. et al. Characterization of human ovarian carcinoma-associated antigens defined by novel monoclonal antibodies with tumor-restricted specificity, *Int J. Cancer*, Mar. 15, 1987, vol. 39, Issue 3, pp. 297-303.

Netti, P. A. et al. Time-dependent behavior of interstitial fluid pressure in solid tumors: implications for drug delivery, *Cancer Res.* Nov. 15, 1995, vol. 55, Issue 22, pp. 5451-5458.

Jain, R.K. Physiological barriers to delivery of monoclonal antibodies and other macromolecules in tumors, *Cancer Res.*, Feb. 1, 1990, vol. 1, Issue 50 (3Suppl.), pp. 814s-819s.

Adams, G.P. et al. High affinity restricts the localization and tumor penetration of single-chain fv antibody molecules, *Cancer Res.*, Jun. 15, 2001, vol. 61, Issue 12, pp. 4750-4755.

King, D.J. et al. Improved tumor targeting with chemically cross-linked recombinant antibody fragments, *Cancer Res.* Dec. 1, 1994, vol. 54, Issue 23, pp. 6176-6185.

Willuda, J. et al. High thermal stability is essential for tumor targeting of antibody fragments: Engineering of a humanized anti-epithelial glycoprotein-2 (epithelial cell adhesion molecule) single-chain Fv fragment, *Cancer Res.* 1999, vol. 59, pp. 5758-5767.

Ewert, S. et al. Biopysical properties of human antibody variable domains, *J. Mol. Biol.* 2003, vol. 3, Issue 5, pp. 531-553.

Tomassetti et al. *J. Cellular Biochemistry*, 1999, vol. 72, pp. 111-118.

Stalteri, M.A. et al. A cross-linked monoclonal antibody fragment for improved tumor targeting, *Bioconjug. Chem.* Mar-Apr. 1995, vol. 6, Issue 2, pp. 19-86.

Sharkey, R.M. et al. A universal pretargeting system for cancer detection and therapy using bispecific antibody, *Cancer Res.* Jan. 15, 2003, vol. 63, Issue 2, pp. 354-363.

Adamczyk, M. et al. Complete sequencing of anti-vancomycin Fab fragment by liquid chromatography—electrospray ion trap mass spectrometry with a combination of database searching and manual interpretation of the MS/MS spectra, *J. Immunol. Methods*, Feb. 1, 2002, vol. 260, Issue1-2, pp. 235-249.

Humphreys, D.P. et al. F(ab')$_2$ molecules made from *Escherichia coli* produced Fab' with hinge sequences conferring increased serum survival in an animal model, J. Immunol. Methods, Aug. 1, 1998, vol. 217, Issue 1-2, pp. 1-10.

Casey, J.L. et al. tumor targeting of humanized cross-linked divalent-Fab' antibody fragments: a clinical phase I//II study, *Br. J. Cancer*, May 6, 2002, vol. 86, Issue 9, pp. 1401-1410.

DeSilva, B.S. et al. Synthesis of bifunctional antibodies for immunoassays, *Methods*, Sep. 2000, vol. 22, Issue 1, pp. 33-43.

Written Opinion for PCT/EP2007/007944 filed on Sep. 12, 2007, in the name of Dompe Pha. R. Ma S.P.A., mail date: Mar. 15, 2009.

* cited by examiner

Alignment of C4 and AFRA light chain amino acid sequences

```
C4    (1)   -QSALTQPASVSGSPGQSITISCTG-TSSDVGSYNLVSWYQQHPGKAPKL
AFRA  (1)   EIVLTQSPASLAVSPGQRATITCRASESVSFLGINLIHWYQQKPGQPPKL

C4    (49)  MIYEGSKRPSGVSNRFSGSKSGNAASLTISGLQAEDEADYYCQSYDSSLS
AFRA  (51)  LIYQASNKDTGVPARFSGSGSGTDFTLTINPVEANDTANYYCLQSKNFPP

C4    (99)  VVFGGGTKLTVLGQPKAAPSVTLFPPSSEELQANKATLVCLISDFYPGAV
AFRA  (101) YTFGQGTKLEIKR-TVAAPSVFIFPPSDEQLKSGTASVVCLLNNFYPREA

C4    (149) TVAWKADSSPVKAG-VETTTPSKQSNNKYAASSYLSLTPEQWKSHRGYSC
AFRA  (150) KVQWKVDNALQSGNSQESVTEQDSKDSTYSLSSTLTLSKADYEKHKVYAC

C4    (198) QVTHEGSTVEKTVAPT--ECS--
AFRA  (200) EVTHQGLSSPVTKSFNRGEC-
```

Figure 1

AFRA kappa light chain (Vκ Cκ) amino acid sequence :

AFRA    (1)   EIVLTQSPASLAVSPGQRATITCRASESVSFLGINLIHWYQQKPGQPPKL

AFRA   (51)   LIYQASNKDTGVPARFSGSGSGTDFTLTINPVEANDTANYYCLQSKNFPP

AFRA  (101)   YTFGQGTKLEIKRTVAAPSVFIFPPSDEQLKSGTASVVCLLNNFYPREA

AFRA  (150)   KVQWKVDNALQSGNSQESVTEQDSKDSTYSLSSTLTLSKADYEKHKVYAC

AFRA  (200)   EVTHQGLSSPVTKSFNRGEC

FIGURE 7

V_H of AFRA

NVQLVESGGGLVQPGRSLRLSCTTSGFTFGDYAMIWARQAPGKGLEWVSSISSSSYIYYADSVKGRFTIS
RDNAKNSLYLQMNSLRAEDTAVYYCARERYDFWSGMDVWGKGTTVTVSS

FIGURE 8

Example of C$_H$1 of AFRA

```
 1  ASTKGPSVFP  LAPSSKSTSG  GTAALGCLVK  DYFPEPVTVS  WNSGALTSGV  HTFPAVLQSS
61  GLYSLSSVVT  VPSSSLGTQT  YICNVNHKPS  NTKVDKK
```

FIGURE 9

A : Folate Receptor alpha

```
MAQRMTTQLL LLLVWVAVVG EAQTRIAWAR TELLNVCMNA KHHKEKPGPE   50
DKLHEQCRPW RKNACCSTNT SQEAHKDVSY LYRFNWNHCG EMAPACKRHF  100
IQDTCLYECS PNLGPWIQQV DQSWRKERVL NVPLCKEDCE QWWEDCRTSY  150
TCKSNWHKGW NWTSGFNKCA VGAACQPFHF YFPTPTVLCN EIWTHSYKVS  200
NYSRGSGRCI QMWFDPAQGN PNEEVARFYA AAMSGAGPWA AWPFLLSLAL  250
MLLWLLS                                                257
```

B : recombinant soluble alpha folate receptor with His6 purification tag

```
                      RIAWAR TELLNVCMNA KHHKEKPGPE   26
DKLHEQCRPW RKNACCSTNT SQEAHKDVSY LYRFNWNHCG EMAPACKRHF   76
IQDTCLYECS PNLGPWIQQV DQSWRKERVL NVPLCKEDCE QWWEDCRTSY  126
TCKSNWHKGW NWTSGFNKCA VGAACQPFHF YFPTPTVLCN EIWTHSYKVS  176
NYSRGSGRCI QMWFDPAQGN PNEEVARFYA AAHHHHHH              214
```

FIGURE 10

HUMAN ANTI-FOLATE RECEPTOR ALPHA ANTIBODIES AND ANTIBODY FRAGMENTS FOR THE RADIOIMMUNOTHERAPY OF OVARIAN CARCINOMA

The present invention concerns high affinity human antibodies and antibody fragments, particularly Fab fragments, specific for the human folate receptor alpha. The invention also concerns methods for producing such antibodies and fragments, and their use in therapeutic and diagnostic settings, such as radioimmunotherapy, particularly in ovarian cancer. The invention further relates to pharmaceutical compositions containing the antibodies and fragments.

Epithelial ovarian cancer (EOC) is the most lethal of gynaecological malignancies in the industrialized countries and in Europe. Despite the relatively low incidence (approximately 1/100,000 new cases each year), EOC presents a high case-fatality ratio and the overall 5-year survival has remained at about 44%[1], [2]. Women with organ-confined tumours have an excellent prognosis, but the majority of early stage cancer is asymptomatic and more than two-thirds of patients are diagnosed with advanced disease. Early-stage EOC is generally asymptomatic and most women (70-75%) present advanced disease, which often spreads as diffuse small-volume tumour deposits. Initial surgery is almost always necessary in the management of suspected ovarian cancer for histological confirmation, staging and tumour debulking. Effective cytoreductive surgery at the time of diagnosis, achievable mainly in early-stage disease, has been correlated with improved survival. However, due to the difficulties in early diagnosis and the propensity for diffuse small-volume disease, the vast majority of EOC patients require adjuvant treatment in the attempt to eradicate residual disease.

Chemotherapy has played an increasingly important role in the effective treatment of ovarian carcinoma[3], [4]. EOC is considered a chemosensitive tumour; in fact 70-80% of EOC patients who receive highly active front-line chemotherapy enter clinical remission. However, despite the development of new therapeutic approaches and the improved median overall survival, relapse occurs in the majority of advanced-stage patients after complete response to initial treatments, and at least 70-90% of these patients eventually die with drug (therapy)-resistant cancers, with only 10-30% showing long-term survival.

There is therefore a great need for alternative treatment methods for ovarian cancer. One of these alternative treatments is radioimmunotherapy. Ovarian carcinoma can be treated with adjuvant radioimmunotherapy to eradicate metastases which are chemo-resistant. Radioimmunotherapy consists in labelling a monoclonal antibody specific for a cancer epitope with a radioactive component. The radiolabelled monoclonal antibody is then injected in vivo and its specificity will lead to its accumulation in the cancer mass. This technique allows the concentration of the therapeutic agent, in this case the radioactive component, in the cancer cells and, contrary to chemo-therapy, which is not site specific, has less toxicity and side effects due to its selective targeting and a possible different mechanism of action, and the lower dosage of therapeutic agent used in the overall treatment.

For ovarian carcinoma several different markers have been so far identified and have generated many different antibodies. Among them, the best characterized are anti-CA125[5],[6] and anti-MUC-1 antibodies, and anti-folate receptor antibodies such as Mov18[7]. The latter present several significant advantages.

Folate receptor alpha ($\alpha$FR) is a glycosyl phosphatidylinositol linked protein with a high affinity for folic acid and some reduced folates such as 5-methyltetrahydrofolate and tetrahydrofolate. It is also present on a limited number of epithelial cells, especially kidney, placenta and choroid plexus but expressed at their apical surface rendering it inaccessible for antibodies. The over-expression of the $\alpha$FR by ovarian carcinoma cells and its restricted distribution in normal tissues provides an opportunity for the development of anti $\alpha$FR antibodies for radioimmunotherapy. MOv18 is a monoclonal antibody which is specific for the alpha folate receptor which is an ideal target for radioimmunotherapy since it is over-expressed in 90% of ovarian carcinomas. MOv18 radiolabelled with $^{131}$I has already been brought, with some success, to phase I/II clinical trial. Other murine monoclonal antibodies raised to $\alpha$FR include MOv19.

A number of other mAbs, including MOV18, have shown efficacy in different clinical trials but have been limited in their clinical development by their murine origin. To circumvent their immunogenicity some antibodies have been engineered to form chimeric or humanized antibodies before or during their clinical development, the last generation being fully human and under clinical development.

A limitation often encountered by radioimmunotherapy is the long antibody half-life which can be of several days. On the one hand, this property can represent an advantage, giving an adequate amount of time to the antibody to target the tumour. However, on the other hand this also means that the patient may have for several days, depending on the label, a radioactive component decaying in the veins throughout the body. In this case the tumour to blood or organ ratio will hardly exceed a log in the most favourable conditions since the antibody slowly clears from the patient's body. From this point of view, reducing the antibody half-life will decrease treatment toxicity by lowering side effects due to the accumulation of unspecific radiations in healthy tissues.

A further point to consider is the tumour penetration. Steric-hindrance of the mAb molecules have no influence as long as the target is an isolated cell in the blood stream, but becomes critical when considering solid tumours as in the case of ovarian carcinoma[8], [9]. Solid tumour penetration is also influenced by the antibody affinity for its ligand and it has been previously demonstrated that a too low affinity prevents tumour localization whereas a too high affinity limits antibody binding to the tumour periphery[10], this latter phenomenon being described as the antigen barrier.

In view of the above considerations (origin, size, half life and affinity) the use of human antibody fragments (Fab) for the radioimmunotherapy of ovarian carcinoma has been proposed. Indeed, a smaller molecule than a full antibody is likely to favour tumour penetration and its human origin should eliminate immunogenic reactions. Moreover, half-life will be shortened. The affinity of such molecules needs to be specifically addressed as a function of the selected antibody fragment. Another advantage of the Fab format is that this type of molecule does not require any glycosylation to be functional. This is compatible with micro-organism production and the associated advantages.

Such an antibody fragment has been generated in the past using guided selection starting from MOv19, a monoclonal antibody (Mab) selected from the same fusion from which MOv18 was generated, recognizing a non-cross-reacting epitope on the same target antigen, i.e. $\alpha$FR. The selected Fab fragment, named C4[11], has been described as being able to specifically bind $\alpha$FR by in vitro assays. C4 exhibited an estimated $K_{aff}$ of 200 nM, by a Scatchard analysis carried out on entire EOC cells.

The development of a C4-Fab fragment suitable for in vivo clinical use in the therapy and diagnosis of ovarian cancer has therefore been envisaged. However, the present inventors have found that the relatively low affinity of the C4 antibody Fab fragment and its in vivo half life are incompatible with the requirements for clinical development. Indeed, in vivo experiments carried out by the inventors with the C4 Fab fragment showed that:

the affinity of the C4 Fab fragment was too low for efficient tumour localization;

the in vivo half life of the C4 Fab was very short, which together with its low affinity, prevented any tumour localization; it was almost impossible to detect the Fab fragment in animal blood even just one hour after intravenous administration. This over-rapid clearance prevented the accumulation of the antibody fragment in the solid tumour leading to inconsistent biodistribution results.

In addition, the inventors discovered that the production of recombinant C4 Fab in E. coli, and its subsequent purification was seriously hampered by the simultaneous production of a non-functional light chain homodimer contaminant ($L_2$) which is difficult to eliminate during purification steps.

The inventors therefore decided to investigate the possibility of producing a dimeric Fab fragment suitable for the radioimmunotherapy of ovarian carcinoma. Shifting from the Fab to the $F(ab')_2$ format gives several advantages, such as bivalency, which increases fragment avidity and therefore its overall affinity, doubles its molecular weight with respect to the corresponding Fab fragment, which in turn decreases excretion in urine protecting kidneys and consequently prolongs its in vivo half-life[12].

The inventors however surprisingly discovered that it was not possible to efficiently dimerize the C4 Fab fragment. Neither natural nor chemical dimerization methods gave rise to acceptable yields of C4 dimer; any small amount of correct dimer product was highly contaminated by incorrect surrogate dimer species which could not be removed by gel filtration chromatography purification. The inventors found that the production of a Fab dimer required extensive modification of the original C4 Fab fragment, including the replacement of the C4 lambda light chain with a kappa light chain. This was done using a guided selection procedure. The new Fab fragment comprising the thus-selected kappa light chain was named AFRA and gave rise to a Fab having improved binding affinity. The new kappa light chain also avoided the problem of light chain homodimer formation, and improved stability, which is advantageous for radioimmunotherapy[13]. A further benefit is the fact that kappa chains are more easily expressed in Escherichia coli[14] which is particularly advantageous in the case of an industrial application. The amino acid sequence of the AFRA kappa light chain of the invention is illustrated in FIGS. 1 and 7 (SEQ ID NO:1). For comparison, the amino acid sequence of the C4 light chain is also shown in FIG. 1 (SEQ ID NO:12).

The present invention thus relates to an antibody, preferably monoclonal, or to a fragment of an antibody, which specifically binds to the folate receptor alpha, wherein the said antibody or fragment comprises a light chain which comprises or consists of the AFRA amino acid sequence illustrated in FIGS. 1 and 7 (SEQ ID NO:1), or a derivative of said light chain having an amino acid sequence which is functionally equivalent to that illustrated in FIGS. 1 and 7 (SEQ ID NO:1). Functional equivalents are as defined hereinafter.

In the context of the present invention the following terminology is used:

the terms "antibodies and fragments of the invention" or "AFRA antibodies" or "AFRA antibody fragments", unless otherwise stated, signify antibodies or fragments which comprise a light chain comprising or consisting of an amino acid sequence which is identical to that illustrated in FIGS. 1 and 7 (SEQ ID NO:1), or an amino acid sequence which is functionally equivalent to that illustrated in FIGS. 1 and 7 (SEQ ID NO:1).

The term "AFRA-derived antibody" or "AFRA-derived antibody fragment" is used to designate antibodies or fragments which comprise a light chain having an amino acid sequence which is functionally equivalent to that illustrated in FIGS. 1 and 7 (SEQ ID NO:1).

The term "AFRA light chain" signifies the light chain illustrated in FIGS. 1 (AFRA) and 7 (SEQ ID NO:1). The term "AFRA-derived light chain" means a light chain having an amino acid sequence which is functionally equivalent to that illustrated in FIGS. 1 (AFRA) and 7 (SEQ ID NO:1).

The term "antibody" is used synonymously with the term "immunoglobulin" (or 'Ig'). Unless otherwise specified the term 'antibody' or the term 'immunoglobulin', signifies an intact (or whole) antibody molecule. Fragments are designated as such.

Numbering of amino acid positions within the antibody molecule is made using the Kabat numbering system (Kabat, H. A., et al. Sequences of Proteins of Immunological Interest, 5th Ed. (U.S. Dept. Health and Human Services, Bethesda, Md., 1991), unless otherwise stated.

In nature, antibodies are glycoprotein molecules produced by B lymphocytes. The antibodies of the invention may be produced by B lymphocytes, by hybridoma, by expression of the recombinant antibody in a prokaryotic or eukaryotic host cell, or by synthetic techniques such as antibody engineering from existing antibodies. They may or may not be glycosylated. Generally speaking, antibodies bind antigens with a high degree of specificity, and can be subdivided on the basis of physical and functional properties into five classes (or isotypes), designated IgG, IgM, IgA, IgD and IgE. These different types of antibodies share a common basic structural unit which has a molecular weight of approximately 150,000 Daltons (150 kDa) and is composed of two identical heavy (H) polypeptide chains and two identical light (L) chains, covalently bonded via interchain disulfide (S—S) linkages between cysteine residues. The intact antibodies of the invention also have this structure. Preferably, they are of the IgG type.

In the context of the present invention, an 'antibody fragment' means any portion of an antibody, preferably an antigen-binding portion, and includes variants of such portions. Examples of antigen-binding fragments according to the invention are Fab fragments; Fab' fragments; $F(ab)_2$ fragments and minibodies. Variants of such fragments include dimers, and trimers of the fragments, and inter-fragment fusions, obtained by use of natural hinge sequences, synthetic hinge sequences, peptide linkers or chemical conjugates. Fragments of the invention may be monovalent (for example Fab fragments), bivalent (for example $F(ab)_2$ fragments) or multivalent (for example a chemical conjugate comprising a trimeric Fab fragment).

The antigen to which the AFRA antibodies and fragments of the invention specifically bind is the human folate receptor alpha (αFR). The folate receptor has three isoforms, alpha, beta and gamma, which show approximately 70% identity in amino acid sequence. These different isoforms display significant differences in their relative affinities for folic acid and are differentially tissue-specific and differentially elevated in several malignancies. The alpha isoform is normally linked to the cell surface by a glycosyl-phosphatidylinositol membrane anchor[15]. It has a high affinity for folic acid, mediating internalization of receptor-bound folate compounds and folate conjugates. Folate receptor alpha has a very restricted distribution in normal tissues (i.e. present on a limited number of normal epithelial cells), but is over-expressed in carcinoma of gynaecological tissues for example in ovarian carcinoma. According to the invention, the term "folate receptor alpha" is synonymous with the following terms: FR-alpha; FRα; Folate receptor 1; Adult Folate receptor; Adult folate-binding protein; FBP; Ovarian tumour-associated antigen MOv18. In the context of the invention, the term encompasses the receptor as expressed on the surface of a cell and also its soluble form. The primary amino acid sequence of human folate receptor alpha is shown in FIG. 10A and a soluble form in FIG. 10B.

An important feature of the antibodies and fragments of the invention is that their binding to the folate receptor alpha is specific. Since the antibodies and fragments of the invention have a reactivity superimposible to those of C4 and Mov19, they do not bind to the beta and gamma isoforms of the folate receptor. The terms "specifically bind" mean that the antibodies and fragments of the invention bind with high affinity (preferably with a $K_D$ of at least 100 nM and most preferably a $K_D$ of at least 20 nM) to FRα, as expressed on the surface of a mammalian cell, and do not bind to proteins having, in the same epitopic region, less than 90% identity, preferably less than 95% identity, and most preferably less than 98% identity. The epitope recognised by the monoclonal antibodies of the invention may be a continuous epitope or may be a discontinuous (conformational) epitope, formed by the receptor when it adopts its native configuration at the surface of a human cell, preferably at the surface of a human ovarian carcinoma cell. For example, the antibodies and fragments of the invention do not bind to proteins having less than 90% overall identity, preferably less than 95% overall identity, and most preferably less than 98% overall identity. It is thus possible that antibodies and fragments of the invention bind to proteins having a very high degree of identity to the human folate receptor alpha shown in FIGS. 10A and B, such as allelic variants having between one and five amino acid differences with respect to the FIG. 10 sequences, and being substantially identical to the FIG. 10 sequences with respect to the epitopic region(s) recognised by the antibodies of the invention.

As indicated above, whilst FRα is over-expressed on ovarian carcinoma cells, it is also expressed on certain types of normal epithelial cells. However, the expression on normal cells is at the apical surface, rendering the receptor inaccessible to the antibodies of the invention in an in vivo context. Consequently, in vivo, the antibodies and fragments of the invention specifically bind to FRα expressed on ovarian carcinoma cells where as a consequence of transformation, cells lose their polarity and alpha folate receptor is then expressed on the whole cell surface (or other carcinoma) and cannot bind to the receptor expressed on the surface of normal epithelial human cells. In contrast, in the case that the antibodies and fragments of the invention are tested by in vitro assays, on isolated normal human epithelial cells or tissues (such as epithelial cells of pituitary, endometrium, thyroid or pancreas) or cell-lines expressing low levels of FRα, a specific binding may be detected.

The AFRA antibodies and AFRA antibody fragments of the invention are characterised by a specific light chain, the amino acid sequence of which is illustrated in FIG. 1 (SEQ ID NO:1). The illustrated AFRA light chain has a structure which is typical of an immunoglobulin light chain (L). Indeed, generally speaking, light chains (L) are approximately 220 amino acids long, and have one variable domain ("$V_L$") at the amino terminal of the light chain (approximately 110 amino acids) and one constant domain ("$C_L$") consisting of the remaining carboxyl half of the L chain. The AFRA light chain of the invention comprises 218 amino acids, the N-terminal 113 amino acids making up the variable region ("$V_L$") and the remaining 105 amino acids of the carboxy terminal making up the constant domain ("$C_L$"). The amino acid sequence of the variable region of the light chain is unique to the AFRA antibody of the invention. Together with the variable region of an associated heavy chain, it forms the antigen binding site of the antibody. The constant region of the AFRA light chain is a typical kappa light chain.

Whilst the light chain of the AFRA antibodies and fragments of the invention is usually identical to that illustrated in FIGS. 1 and 7, certain changes can nevertheless be made to this sequence without departing from the invention. Indeed, the invention also relates to "AFRA-derived antibodies" or "AFRA-derived antibody fragments" which comprise a light chain which is functionally equivalent to that illustrated in FIGS. 1 and 7 (SEQ ID NO:1). Such a functionally equivalent light chain is an amino acid sequence which:

comprises a light chain whose variable region comprises at least one of the regions of the AFRA light chain illustrated in FIGS. 1 and 7 which determines specificity for the folate receptor alpha, and a kappa constant region. The regions determining specificity correspond to the "hypervariable" regions of the $V_L$ chain, also called "complementarity-determining regions" (CDRs). These CDRs are designated CDR1, CDR2 and CDR3 or alternatively L1, L2 and L3. The complementarity determining regions, confirmed by the Fab crystal structure, of the AFRA sequence (SEQ ID NO:1) are:

| | |
|---|---|
| RASESVSFLGINLIH, | (SEQ ID NO: 3) |
| QASNKDT, | (SEQ ID NO: 4) |
| LQSKNFPPYT, | (SEQ ID NO: 5) |

These regions are illustrated in FIG. 7 in bold type, underlined. Thus, according to this variant of the invention, the AFRA-derived antibody or AFRA-derived antibody fragment, specifically binds to folate receptor-alpha (FRα) and comprises a light chain whose variable region comprises at least one, and preferably two, and most preferably all three of the following amino acid sequences:

| | | |
|---|---|---|
| CDR1: | RASESVSFLGINLIH, | (SEQ ID NO: 3) |
| CDR2: | QASNKDT, | (SEQ ID NO: 4) |
| CDR3: | LQSKNFPPYT. | (SEQ ID NO: 5) |

The CDR sequences listed above are preferably present in the AFRA-derived light chain at the same positions as those in the original AFRA light chain i.e. CDR1: 24-38; CDR2: 54-60; CDR3: 93-102 (using the Kabat numbering system). The remaining sequence of the variable region of the said AFRA-derived light chain can be any framework sequence, for example a framework sequence which differs from the sequence of FIGS. 1 and 7 (SEQ ID NO:1) by the substitution, deletion or insertion of up to ten or twenty amino acids, for example 1, 2, 3, 4 or 5 amino acids, and which, when used to replace the AFRA light chain framework sequence illustrated in FIG. 1, in an antibody or antibody fragment containing the AFRA CDRs, does not qualitatively modify the specificity of the antibody or fragment thereof for the human folate receptor alpha. In one embodiment, the variable region of the AFRA derived light chain differs from the sequence of FIGS. 1 and 7 (SEQ ID NO:1) by the substitution, deletion or insertion of up to ten or twenty amino acids, for example 1, 2, 3, 4 or 5 amino acids, which substitutions, deletions or insertions may take place inside or out of the CDRs. The constant region of said AFRA-derived light chain is a classical kappa constant region, for example identical to amino acids 114 to 219 of the FIG. 7 AFRA sequence (double underlined). Preferably these AFRA-derived antibodies or AFRA-derived antibody fragments bind to folate receptor-alpha (FRα) with an affinity ($K_D$) of less than 50 nM, preferably less than 20 nM.

The specificity of the AFRA-derived antibodies or AFRA-derived antibody fragments as defined above, for the folate receptor alpha can be tested in vitro and/or in vivo using conventional experimental means to show reactivity with the FRα, and absence of cross reactivity with receptor proteins having less than 90% sequence identity, preferably less than 95% sequence identity.

Irrespective of whether the light chain (L) is the unaltered AFRA sequence of SEQ ID NO:1, or a derivative thereof as described above, the antibody or fragment according to the invention preferably further comprises at least a part of an antibody heavy chain, for example at least the variable region ($V_H$), with or without the first constant region, commonly designated $C_{H1}$. Other portions of the heavy chain which may be associated with the light chain of the invention are heavy chain fragments comprising the variable region ($V_H$), the first constant region ($C_{H1}$) and all or part of the hinge region. Alternatively, the heavy chain may be intact, comprising in sequence: $V_H$, $C_{H1}$, the hinge region, $C_{H2}$, $C_{H3}$ and optionally $C_{H4}$. The association between the heavy chain and the light chain is normally covalent, via disulfide linkage involving a cysteine at the carboxy terminal of the light chain.

In the context of the invention, the different segments of a heavy chain which may be associated with the AFRA light chain are defined as follows, bearing in mind that an intact immunoglobulin heavy chain (H) is usually about 440 amino acids long: the variable domain ($V_H$) is the amino terminal stretch of the heavy chain (usually around 110 amino acids). The remainder of the heavy chain comprises three or four (depending on the heavy chain class) repeats of approximately 110 amino acids that have high (at least 30%) sequence homology within a given class. These regions are the constant regions of the heavy chains, designated $C_{H1}$, $C_{H2}$, $C_{H3}$ and $C_{H4}$. The heavy chain also contains a hinge region situated between the $C_{H1}$ and $C_{H2}$ domains, conferring flexibility, and the capacity to form interchain disulfide bonds to the molecule. The hinge allows the two antigen-binding regions of each antibody molecule to move independently to bind antigen.

The variable region of the heavy chain contains three hypervariable regions, again called "complementarity-determining regions" (CDRs), designated H1, H2 and H3, or alternatively CDR1, CDR2 and CDR3. The CDRs of the heavy chain have a length of about 3 to 25 amino acids and play an important role in antibody specificity.

Five different H chains exist in nature, designated alpha (α), gamma (γ), delta (δ), epsilon (ε), and mu (μ), which differ from each other in amino acid sequence. The isotype of a given antibody (i.e. whether it belongs to the IgA, IgG, IgD, IgE, or IgM class) is determined by the H chain of the antibody in question, the alpha H chain defining the IgA isotype, the gamma H chain defining the IgG isotype and so-on. Within the IgG class there are four sub-classes designated IgG1 to IgG4. According to the invention, the heavy chain of the AFRA antibody or fragment or derivative thereof may be any one of these isotypes, but the IgG isotype is particularly preferred, for example IgG1.

Depending upon the particular sub-regions of the heavy chain which are present together with the AFRA light chain, and further depending upon how many sub-units are associated together, the antibody and antibody fragments of the invention may take the form of intact antibodies, or alternatively may be antigen-binding fragments thereof such as Fab fragments, Fab' fragments, F(ab)$_2$ fragments etc.

According to a particularly preferred embodiment of the invention, the AFRA antibody, or AFRA-derived antibody or fragment, is a Fab fragment, comprising or consisting of:
  i) the AFRA light chain (both the variable ($V_L$) and constant regions ($C_L$)), as shown in FIGS. 1 or 7 (SEQ ID NO: 1) or derivative thereof as defined above, and
  ii) the variable region ($V_H$) and first constant region ($C_{H1}$) of a heavy chain.

Preferably, the light chain and heavy chain are covalently bound together by a disulfide bond involving the carboxy-terminal cysteine in the light chain. Fab fragments of the invention typically have a size of around 55 kDa.

A particularly preferred example of this embodiment of the invention is a Fab fragment wherein the variable region of the heavy chain ($V_H$) has the amino acid sequence of FIG. 8 (SEQ ID NO: 2). Alternatively, the variable region of the heavy chain ($V_H$) may have an amino acid sequence which comprises at least one, and preferably two or three of the CDR regions of the illustrated sequence, in a framework sequence which is different from that illustrated in FIG. 8. The CDR regions of the FIG. 8 sequence are the following

```
CDR1    DYAMI               (SEQ ID NO: 6)

CDR2    SISSSSSYIYYADSVKG   (SEQ ID NO: 7)

CDR3    ERYDFWSGMDV         (SEQ ID NO: 8)
```

Another particularly preferred example of this embodiment of the invention is a Fab fragment wherein the constant region of the heavy chain ($C_{H1}$) region is the $C_{H1}$ region of a gamma heavy chain, particularly a gamma1 heavy chain. An example of a typical $C_{H1}$ heavy chain is illustrated in FIG. 9 (SEQ ID NO:9).

Accordingly, a preferred Fab fragment of the invention comprises or consists of the following sequence elements:
  i) a light chain having the amino acid sequence of SEQ n°1,
  ii) a heavy chain, the variable region of which has the amino acid sequence illustrated in FIG. 8 (SEQ ID NO: 2) and the first constant region ($C_{H1}$) of which has the amino acid sequence illustrated in FIG. 9 (SEQ ID NO: 9).

According to another aspect of the invention, the antibody fragment may be a Fab' fragment. In the context of the invention, a Fab' fragment is a Fab fragment in which the heavy chain additionally comprises the natural hinge region on its carboxy terminal, suitable for covalent bonding to a second antibody fragment. The hinge contains one or more amino acid residues or chemical groups which are suitable for covalent bond formation, for example a free cysteine, thereby allowing dimerisation of the Fab' fragment. The hinge region may be at least part of an antibody natural hinge region, for example a hinge region naturally occurring in any one of the alpha (α), gamma (γ), delta (δ), epsilon (ε), and mu (μ) heavy chains. Particularly preferred are hinge regions, or portions thereof, corresponding to the natural sequence of the gamma sub-class, particularly gamma1, such as the pentapeptide DKTSC, or the hexapeptide DKTHTC. The portion of the hinge region used for creation of the Fab' fragment typically contains at least one free cysteine residue, for example at the carboxy terminus, but may be engineered to contain two or three free cysteine residues.

Alternatively, the Fab' fragment may be artificially dimerized by for example a non-proteinaceous moiety such as a chemical linker which confers resistance to hydrolysis in an in-vivo environment. An example of such an artificial linker is bismaleimide ethane (BMOE) but several other linkers have been reported in the literature[16], [17].

The advantage of using Fab' fragments is that they can be dimerised to form F(ab')$_2$ fragments having two antigen binding domains. F(ab')$_2$ fragments are therefore divalent, increasing avidity of binding with respect to a Fab monomer. The two Fab' fragments which compose the dimer are joined together by bonding between each of the two hinge regions, of the Fab' heavy chains. Fab' monomers can be dimerized by the natural oxidation of the free cysteines on the C-termini of the heavy chains. F(ab')$_2$ fragments typically have a size of around 100 to 110 kDa.

If dimerized by a non-proteinaceous artificial linker, the two Fab' monomers making up the F(ab')$_2$ dimer are covalently linked to each other through this chemical linker. For example, a bismaleimide ethane (BMOE) gives rise to a maleimide linkage which is non-hydrolysable, and therefore confers stability on the dimer in an in vivo environment.

According to this aspect of the invention, the two antigen binding domains of the F(ab')$_2$ dimer may have identical specificities, both specifically binding to a given epitope of folate receptor alpha. Alternatively, the F(ab')$_2$ dimer may be bispecific, one of the antigen binding domains being specific for a first epitope of folate receptor alpha, and the other being specific for a second epitope of folate receptor alpha. A further possibility is that the second antigen binding domain binds to an antigen entirely distinct from folate receptor alpha, such as a second carcinoma antigen or to a natural killer marker of effector cells.

The antibodies and fragments of the invention are preferably fully human. The AFRA light chain of the invention is of human origin. It is therefore advantageous to combine the light chain with a heavy chain of human origin. Alternatively, the AFRA light chain may be initially combined with a heavy chain of non-human origin, for example murine, and then antibody engineering techniques may be used to humanise the heavy chain.

The antibodies and fragments of the invention are characterised by a high binding affinity and avidity for the human folate receptor alpha. Binding affinity is the strength of the interaction between a single antigen-binding site on an antibody, or fragment thereof, and its specific antigen epitope. The higher the affinity, the tighter the association between antigen and antibody or fragment, and the more likely the antigen is to remain in the binding site. The term "avidity" is used to describe the overall strength of interaction between an antibody or antibody fragment, and depends on both the affinity and the valency of interactions. The more antigen-binding sites an individual antibody molecule has, the higher its avidity for the antigen.

Affinity can be expressed as an affinity constant $K_A$ which is the ratio between the rate constants for association ($k_{ass}$) and dissociation ($k_{diss}$) of antibody and antigen. $K_A$ is measured in $M^{-1}$; the higher the affinity, the higher the $K_A$.

Alternatively, affinity can be expressed as a dissociation constant $K_D$, wherein $K_D=1/K_A$. The units of $K_D$ are M, and the higher the affinity, the lower the $K_D$. In the context of the invention, affinities are normally expressed as $K_D$. Since most methods of measuring affinity take account of the number of binding sites of an antibody or fragment, $K_A$ and $K_D$ affinity values in fact can be considered to reflect affinity for monovalent antibodies or fragments, and avidity for multivalent antibodies or fragments.

The AFRA antibodies and fragments of the invention preferably bind to folate receptor-alpha (FRα) with an affinity ($K_D$) in the range of 100 nM to 1 pM. More particularly, they have an affinity ($K_D$) of less than 75 nM, preferably less than 50 nM, more preferably less than 30 nM and most preferably less than 5 nM. By way of example, the monovalent fragments of the invention, such as Fab fragments typically show a $K_D$ of less than 50 nM. This affinity represents a considerable improvement over the known monomeric C4 Fab fragment. The divalent fragments of the invention such as F(ab')$_2$ or a Di Fab Maleimide (DFM) typically show a $K_D$ of less than 30 nM, for example less than 5 nM. These values can be obtained using either soluble receptor or cell surface-expressed receptor as antigen.

In accordance with the invention, binding affinity can be measured by a number of conventional techniques, such as equilibrium dialysis, with Scatchard analysis of the data, according to which:

$$r/c=K(n-r),$$

wherein:
r=moles bound ligand/mole antibody at equilibrium;
c=free ligand concentration at equilibrium;
K=equilibrium association constant; and
n=number of antigen binding sites per antibody molecule (valence)

ELISA competition binding assays can also be used for the determination of $K_A$, again using Scatchard analysis. Alternatively, the relative $K_D$ can be determined as the concentration at which half of the ELISA plateau signal is obtained.

A further technique which may be used to measure binding affinity is surface plasmon resonance (SPR), for example using Biacore technology (Pharmacia). With this method it is possible to measure binding kinetics as well as affinity constants. According to this technique, $K_D=k_{diss}/k_{ass}$ where $k_{diss}$ is the dissociation rate constant (also designated $k_{off}$), and $k_{ass}$ is the association rate constant (also designated $k_{on}$).

According to the invention, the antigen used in the affinity analyses may be the folate receptor alpha as expressed on the surface of whole cells, particularly human cells, for example human ovarian carcinoma cells such as OVCAR3 (ATCC), IGROVI (gift provided by Dr J. Bénard, Institut Gustave Roussy, Villejuif, France) or cells transfected with the human folate receptor alpha such as A431-Fr cells[18]. Alternatively, the antigen may be in the form of a soluble receptor for example recombinant FRα as shown in FIG. 10. The use of soluble receptor is particularly advantageous for surface plasmon resonance (SPR) analysis, and may be used to predict binding in vivo in humans.

The AFRA antibodies and fragments of the invention can be used in a number of therapeutic, diagnostic and imaging applications. The invention thus relates to an AFRA antibody or fragment according to the invention for the treatment of disorders involving over-expression of folate receptor-alpha (FRα). In particular, the AFRA antibodies and fragments of the invention can be used for the preparation of a medicament for the treatment of disorders involving over-expression of folate receptor-alpha (FRα), such as cancer. An aspect of the invention thus relates to a method for treating a disorder involving over-expression of folate receptor-alpha (FRα), said method comprising administering to a subject in need of such treatment, an effective amount of an AFRA antibody or fragment according to the invention.

For many of the therapeutic, diagnostic and imaging applications, the antibody or fragment is conjugated to an effector moiety such as a cytotoxic agent or marker. This is the case for treatment of disorders such as carcinoma, for example gynaecological carcinoma.

A particularly preferred therapeutic use of the AFRA antibodies and fragments is in radioimmunotherapy of ovarian carcinoma in humans. For such an application, the antibodies and fragments are conjugated to a cytotoxic radionuclide, such as $^{131}$I, $^{90}$Y, $^{177}$Lu, $^{188}$Re. A most preferred radionuclide is $^{131}$I. Moreover, other radionuclides such as $^{99}$Tc may be used for example in a diagnostic or imaging setting.

The AFRA antibodies and fragments are particularly well suited to radioimmunotherapy on account of their low $K_D$ value for the alpha folate receptor, significantly improved over the known C4 Fab. The higher affinity of the AFRA antibodies and fragments with respect to the affinity of C4 represents a real advantage for radioimmunotherapy since this directly influences tumour localization and antibody dosage. In this particular case the higher affinity of the AFRA antibodies and fragments directly reflects the amount of tumour-bound antibody. In other words, since the AFRA antibodies and fragments have $K_D$ value much lower than C4, the AFRA molecules will, at the same dilution, reach a higher concentration in tumour tissues than C4 would do. This reduces background and consequently also reduces treatment side effects which are mainly due to antibody unspecific binding. Radioimmunotherapy is effectively based on the specific accumulation of radioactivity in the tumour, and the higher ratio of tumour/healthy tissues obtained with the AFRA antibodies and fragments provides a clear pointer to improved therapeutic effect.

The conjugation of the radionuclide to the antibodies or fragments of the invention can be made using any conventional techniques such as the use of a linker between the antibody and the radioisotope. Preferably, the radioimmunoconjugate has a specific activity of from about 0.5 to about 15 mCi/mg, depending on the radionuclide, and may be administered via an intravenous or other route. Depending on the desired duration and effectiveness of the treatment, the radionuclide-antibody conjugates of the invention may be administered once or several times, in combination with other therapeutic drugs or radio-sensitizing agents. The amount of the radioimmunoconjugate applied depends on the precise nature of the carcinoma. The dose of radioactivity per administration must be high enough to be effective, but must be below the dose limiting toxicity (DLT). Single administrations are preferred; multiple administrations are also possible. In general, the radioactivity dose per administration will be between 20 and 80 mCi/m2 body surface area (BSA).

According to a preferred embodiment of the invention, the AFRA antibody fragment used for radioimmunotherapy is a dimeric fragment, for example F(ab')$_2$ or a chemical Fab dimer such as F(ab')$_2$-DFM. Typical AFRA Fab dimers for radioimmunotherapy applications comprise the AFRA light chain in association with an IgG heavy chain, having a variable region such as the one illustrated in FIG. 8, or a variable region comprising the CDRs of the FIG. 8 sequence in a different framework sequence.

The antibodies and fragments of the invention can be used as single therapeutic agents in the treatment of disorders such as cancer, particularly ovarian cancer. Alternatively, they can be used in association with other therapeutic agents, in combined therapy involving multiple drugs and/or treatment methods. For example, the antibodies or fragments of the invention can be used together with chemotherapy, radiation therapy, hormone therapy or biological therapy.

This embodiment of the invention thus relates to a product containing an antibody or fragment according to the invention and at least one further therapeutic agent, as a combined preparation for simultaneous, separate or sequential use in therapy. A further therapeutic agent is typically selected from the group consisting of a chemotherapeutic agent and a radiotherapeutic agent. Such products for combined therapy are particularly suitable for treatment of human cancer, for example ovarian cancer.

In the context of such combination therapy, the antibodies or fragments of the invention may be used as the primary treatment in association with a suitable secondary treatment, which is administered simultaneously with, or successively to the AFRA antibodies or fragments. Alternatively, the antibodies or fragments of the invention may be used as the secondary treatment to assist the primary treatment, such as chemotherapy. This aspect of the invention thus includes a method for treating a disorder involving over-expression of folate receptor-alpha (FRα), said method comprising administering to a subject in need of such treatment, an effective amount of a first therapeutic agent and an effective amount of a second therapeutic agent, wherein the first and second therapeutic agents are administered to the subject simultaneously, sequentially or separately, and the first or second therapeutic agent comprises an AFRA antibody or fragment according to the invention.

The antibodies or fragments of the invention can thus be used for performing adjunctive or adjuvant therapy with a further therapeutic agent, for example a chemotherapeutic agent, for treatment of human cancer, particularly ovarian cancer.

According to a further aspect of the invention, the AFRA antibodies or fragments may be present together with other antibodies or fragments, in the form of a cocktail or mixture. These other antibodies or fragments may be further AFRA antibodies or fragments, specific for the folate receptor alpha, or may be antibodies or fragments having specificity towards a different antigen. The cocktails or mixtures of the invention also include mixtures of AFRA antibodies or fragments comprising different AFRA antibody formats such as mixtures of monomeric and dimeric AFRA fragments or fragments having at least one light chain with the AFRA amino acid sequence illustrated in FIG. 1 or 7 (SEQ ID NO:1), or the functional equivalent of said light chain.

The invention thus includes mixtures of AFRA antibodies or fragments, which mixture comprises a heterogeneous composition of antibody fragments comprising or consisting of:

i) divalent antibody fragments specifically binding to the human folate alpha receptor, said divalent fragments comprising two covalently linked Fab' fragments each having a light chain having the AFRA amino acid sequence illustrated in FIG. 1 or 7 (SEQ ID NO:1), or the functional equivalent of said light chain, and ii) further antibody fragments comprising at least one light chain having the AFRA amino acid sequence illustrated in FIG. 1 or 7 (SEQ ID NO:1), or the functional equivalent of said light chain, the divalent antibody fragment (i) comprising at least 50%, preferably at least 60% and most preferably at least 70% of the composition. Preferably, the fragments (ii) account for less than 20% of the composition, most preferably less than 10%.

The bivalent species may be natural dimers, joined by disulfide linkages between the hinge regions of the Fab' fragments or may be chemical dimers such as DFM-AFRA.

For example, in conditions of natural dimerisation, around 80% of the AFRA dimerization product is found to be F(ab')$_2$ after purification. The high proportion of antigen-binding dimers formed by the AFRA fragments of the invention constitutes a further advantage compared to the known C4 Fab. The inventors have observed that a pseudo dimer is formed during dimerisation. This pseudo-dimer is composed of two light chains covalently linked to one heavy chain and a second heavy chain is maintained in the structure through hydrophobic interactions. Since this pseudo dimer can be resolved in SDS-PAGE into two species one of 75 kDa (L$_2$H) and another one at 25 kDa (heavy chain) it was called L$_2$H for simplification. During 'natural' dimerisation of the C4 Fab', the correct dimer, L$_2$H$_2$, only represents about 30% of the reaction product whereas the remaining 70% of the material corresponds to the L$_2$H dimer. It is not possible to chromatographically purify the C4 dimer from its surrogate and since the percentage of pseudo dimer is far higher than the one of the correct dimer, the development of the C4 molecule for radioimmunotherapy is not feasible.

For dimers obtained by chemical dimerisation the AFRA fragments give rise to dimerisation product mixtures having at least 50% F(ab')$_2$. An L$_2$H species may be present, accounting for less than 20% of the composition, most preferably less than 10%, and a heterogeneous composition exists in purified form if the two forms cannot be separated by chromatographic methods. In spite of the presence of the L$_2$H species, the heterogeneous AFRA-DFM mixtures have been shown to have high binding affinity for the human folate alpha receptor, for example with a KD of less than 50 nM, preferably less than 30 nM and most preferably less than 5 nM.

The strong tendency of the C4 light chain to react during "natural" dimer formation is even more pronounced during chemical dimer synthesis (DFM) and almost prevents any dimer assemblage, even when several conditions of pH and temperature are tested. The C4 chemical dimerisation reaction gives a yield of less than five per cent, of which only about 30% is the correct dimer. The overall % of dimer obtained at the end of the reaction is thus ten times lower than for AFRA. This peculiar property together with the low affinity of the C4 Fab, which cannot be used as a monomer, prevents development of the C4 antibody fragment for radioimmunotherapy.

A further aspect of the invention relates to a nucleic acid molecule comprising a sequence which encodes the light chain of an antibody or fragment thereof specifically binding to folate receptor-alpha (FRα), wherein said light chain comprises the amino acid sequence of SEQ ID NO:1, or functional equivalent thereof. The nucleic acid may be DNA or RNA; and may be double-stranded or single-stranded.

The invention also concerns an expression vector comprising the said nucleic acid sequence, wherein the said nucleic acid coding sequence is operably linked to transcription regulatory signals, thereby permitting expression of the AFRA light chain in a suitable host cell. The nucleic acid may further comprise a sequence encoding an antibody heavy chain or fragment thereof, for example in a bicistronic arrangement, facilitating the natural association of the light and heavy chains in the host cell.

The invention also extends to host cells containing a nucleic acid encoding the AFRA light chain, for example a host cell transformed with the expression vector of the invention. The host cells may be prokaryotic, or eukaryotic. As an example of prokaryotic host cells, *Escherichia coli* is particularly preferred. Example of suitable eukaryotic cells include human, primate, murine or yeast cells.

A particularly preferred cell is the strain of *E. coli* deposited with the CNCM on 15 Mar. 2006 under the terms of the Budapest treaty with accession number CNCM I-3586. This micro-organism (*Escherichia coli* strain BW25113 PyrC:: kan (lacI$^q$, rrnB$_{T14}$, ΔlacZ$_{WJ16}$, hsdR514, ΔaraBA-D$_{AH33}$, ΔrhaBAD$_{LD78}$)) contains plasmid DoB0134 and produces an AFRA Fab of the invention. The AFRA Fab fragment obtainable from this deposited strain is also within the scope of this invention.

The invention also relates to a method for producing high affinity human antibodies or fragments thereof, said antibodies or fragments thereof specifically binding to folate receptor-alpha (FRα), wherein said method comprises the steps of:
  transfecting an expression vector as described above in a suitable host cell;
  recovering the expressed AFRA antibody or fragment thereof;
  optionally mutating and/or dimerising the recovered antibody or fragment thereof.

Mutation of the thus expressed antibody or fragment can be carried out to add hinge portions or cysteine residues, or can be used to fine-tune or modulate affinity and specificity of the antibody/fragment.

In one embodiment, the expression vector is co-expressed in the cell with a second expression vector comprising a nucleic acid sequence encoding an antibody heavy chain or fragment thereof, said nucleic acid being operably linked to transcription regulation signals.

An alternative method for producing the antibodies of the invention comprises the steps of:
  construction of the human V$_H$C$_H$ repertoire; the human repertoire is preferably constructed from human B cells, obtained either from bone marrow, lymph nodes, spleen or peripheral blood from patients with ovarian carcinoma, but who are preferably free of the disease at the time of repertoire construction, or alternatively from healthy donors. The repertoire can also be generated by synthesis.
  selection of a human antibody heavy chain having the capacity to specifically bind to folate receptor-alpha (FRα), said selection being carried out by guided selection using an antibody fragment comprising a light chain having the amino acid sequence of SEQ ID NO:1 as the guiding template on a human V$_H$C$_H$ repertoire, followed by selection on human cells over-expressing αFR or on the soluble αFR protein
  expression of a gene encoding the selected human antibody heavy chain together with a gene encoding the light chain having the amino acid sequence of SEQ ID NO:1 in a suitable host cell in conditions permitting the assembly of the said light and heavy chains.

In one embodiment, the gene encoding the selected human antibody heavy chain and the gene encoding the light chain having the amino acid sequence of SEQ ID NO:1, are expressed in the cell by an expression vector comprising a nucleic acid sequence encoding the selected human antibody heavy chain and the amino acid sequence of SEQ ID NO:1 operably linked to transcription regulation signals.

In an alternative embodiment, the gene encoding the selected human antibody heavy chain is expressed in the cell by a first expression vector comprising a nucleic acid sequence encoding the selected human antibody heavy chain operably linked to transcription regulation signals, and the gene encoding the light chain having the amino acid sequence of SEQ ID NO:1 in the cell is expressed by a second expression vector comprising a nucleic acid sequence encoding the AFRA light chain operably linked to transcription regulation signals.

This method allows selection of different heavy chains which create binding domains specific for the folate-receptor alpha when combined with the AFRA light chain. Specific details of this type of method are provided in the examples below.

A further aspect of the invention relates to a pharmaceutical composition comprising the antibody or fragment of the invention, in association with a pharmaceutically acceptable carrier. In such a composition, the antibody or fragment thereof may be conjugated to an effector moiety such as a cytotoxic agent, for example a radionuclide such as $^{131}I$, $^{90}Y$, $^{177}Lu$, $^{188}Re$, or to a toxin, or to a chemotherapeutic agent or to a prodrug or to an enzyme, commonly used linked to antibodies. $^{99}Tc$ can be used in diagnostic applications.

The invention also relates to a method for the diagnosis or imaging of ovarian carcinoma or metastases thereof, comprising for example contacting a tissue, or sample thereof, of a subject with an antibody or fragment according to the invention, said antibody or fragment being conjugated to a suitable label such as a radionuclide. The diagnosis or imaging process can be carried out in vivo, where detection of significant binding of the antibody to the tissue indicates the presence of over-expression of folate-receptor alpha, suggesting malignant transformation of the cells. Alternatively the diagnosis or imaging process can be carried out outside the body, for example in vitro, on a biological sample such as a tissue sample, obtained from the subject. In this latter case, comparison of the level of binding of the antibodies or fragments of the invention to the level of binding observed with a sample of normal tissue is recommended in order to account for detection of any apical expression of folate-receptor alpha in normal, non-transformed cells of such a tissue.

Various aspects of the invention are illustrated in the Figures:

FIG. 1: Alignment of C4 (SEQ ID NO:12).and AFRA (SEQ ID NO:1) light chain amino acid sequences. The AFRA light chain comprises 218 amino acids, of which the first 113 amino acids constitute the kappa variable region, and the remaining 105 amino acids represent the kappa constant region. The main differences between C4 and AFRA antibodies lies in the CDRs.

FIG. 2: Schematic representation of bicistronic expression vector DoB0134, suitable for expressing AFRA Fab in *E. coli*. This vector, containing the nucleic acid sequences encoding the AFRA light chain illustrated in FIG. 1 (SEQ ID NO:1) and the AFRA heavy chain (including a Q1N mutation), contained in *E. coli*, was deposited on 15 Mar. 2006 at the CNCM under accession number CNCM I-3586. BW25113 PyrC::Kan (lacI$^{q}$, rrnB$_{T14}$, ΔlacZ$_{WJ16}$, hsdR514, ΔaraBA-D$_{AH33}$, ΔrhaBAD$_{LD78}$.

FIG. 3 (BIAcore binding): Determination of antibody fragments binding parameters on alpha folate receptor. For this several concentrations of Fab monomer (from 3 to 200 nM) were flowed in the sensorchip cell previously coated with the recombinant receptor and binding was registered for 30 minutes. After this time period washing was monitored for another twenty minutes. For AFRA the $K_D$ was determined to be 43.9 nM with a Chi2 of 1.85 (panel A) whereas for C4 the determined $K_D$ was 168 nM with a Chi2 of 2.19 (panel B).

FIG. 4 (natural dimerization): Fab AFRA and C4 were mildly reduced and gently oxydized to obtain natural dimers. The reaction products were analysed by SDS-PAGE and results are reported in the upper A panel for AFRA with its relative densitometry analysis, whereas panel 8 corresponds to C4. The generation of the $L_2H$ species is reported in the C panel cartoon. Before dimerization, an end portion of $C_{H1}$ has the sequence of CDKTSC (SEQ ID NO: 13). After dimerization, a $C_L$, is linked to a $C_{H1}$ through the sequence of CCSTKDC (SEQ ID NO: 14).

FIG. 5 (Immunohistochemistry): The anti CA125 monoclonal antibody was probed as internal positive control on a human biopsy corresponding to an ovarian carcinoma (A panel). In the same way AFRA-DFM (0.5 g/ml) was assessed on the same tissue (B panel). Both antibodies were FITC and background was estimated on the C slide.

FIG. 6: (Biodistribution of AFRA-DFM-$^{131}I$). The Di-Fab-Maleimide radiolabelled with $^{131}I$ was injected iv in tumour bearing mice. Animals were sacrificed at 1, 3, 6, 15, 24 and 48 hours post injection. Tumour, blood and predefined organs were isolated, weighed and counted to determine the concentration of the AFRA-DFM. The result of the biodistribution is reported in the figure below as the percentage of the injected dose per gram.

FIG. 7: AFRA kappa light chain amino acid sequence (SEQ ID NO:1) showing:
- Variable region ($V_\kappa$) extending from amino acids 1 to 113;
- hypervariable regions as confirmed from crystal structure: CDR1 (amino acids 24 to 38), CDR2 (amino acids 54 to 60) and CDR3 (amino acids 93 to 102) (bold, underlined);
- Kappa constant region ($C_\kappa$) extending from amino acids 114 to 219 (double underlining).

FIG. 8: AFRA Heavy chain (variable region) amino acid sequence (SEQ ID NO:2):
- Variable region ($V_\kappa$) extending from amino acids 1 to 120;
- hypervariable regions: CDR1 (amino acids 31-35), CDR2 (amino acids 50-66) and CDR3 (amino acids 99-110) (bold, underlined);

FIG. 9: AFRA Heavy chain (constant region: IgG1 CH1) (SEQ ID NO:8)

FIG. 10 (Alpha Folate Receptor):

A: Amino acid sequence of the Folate Receptor alpha (SEQ ID NO:10):
- Signal sequence: amino acids 1 to 24
- Mature receptor sequence: amino acids 25 to 234
- Propep sequence: amino acids 235 to 237, removed in the mature form
- Glycosylation sites; amino acids 69, 161 and 201.

B: recombinant soluble alpha folate receptor with His6 purification tag (SEQ ID NO:11).

FIG. 11: In vivo efficacy of radio-labeled AFRA-DFM in xenografted tumours in mice at an average dose of 1 mCi/mouse. Black bars: tumour of A431 cells transfected with human folate receptor alpha (A431FR). Diagonally shaded bars: tumour of A431 cells not transfected with human folate receptor alpha (A431). Open bars: control.

FIG. 12: In vivo localization following i.p. administration. The AFRA-DFM radiolabelled with $^{131}I$ was injected i.p. (average dose=0.074 mCi/mouse) in mice bearing i.p. growing IGROV1 tumour cells. Animals were sacrificed at 1, 3, 6, 15, and 24 hours post injection. Ascite, solid i.p. tumour masses, blood and predefined organs were isolated, weighed and counted to determine the concentration of the AFRA-DFM. The result of the biodistribution is reported as the percentage of the injected dose per gram.

FIG. 13: In vivo efficacy of radio-labeled AFRA-DFM in xenografted ovarian cancer cells in mice. A: overall survival of mice injected i.p. with IGROV1 cells, naturally overexpressing human folate receptor alpha, and treated i.p. at day +2 with 1 mCi/mouse of $^{131}$I-DFM-AFRA or saline (control). B: overall survival of mice injected i.p. with OVCAR3 cells, naturally overexpressing human folate receptor alpha, and treated i.p. at day +2 or +4 with 1 mCi/mouse of $^{131}$I-DFM-AFRA or saline (control).

EXAMPLES

1. Production of a High Affinity Human Fab Fragment Specific for the Alpha Folate Receptor Significant modifications were made to the C4 Fab fragment in order to obtain a human Fab fragment with improved binding characteristics, including increased binding affinity. These modifications are described below:

a) Chain Shuffling: Selection of a Kappa Light Chain Specific for the Alpha Folate Receptor It was first decided to substitute the C4 lambda light chain with a kappa one. The Fab light chain substitution was performed as previously described for the C4 fragment by phage display guided selection ([11]).

Specifically, an antibody kappa light chain ($V_\kappa C_\kappa$) library was generated from human B-cells.

The library was derived from pooled mRNA from peripheral blood lymphocytes obtained from four women who had previously had ovarian carcinoma, but who were disease-free at the time of blood withdrawal. The women had had disease-free status for several years prior to blood collection. Three of the women had had carcinoma of the serous histotype, diagnosed at stage III or IV of the disease. The fourth patient had had ovarian carcinoma of the endometroid histotype, diagnosed at stage III. Between $2.0 \times 10^7$ and $5.0 \times 10^7$ PBMC were collected from each patient for the preparation of the library. Each chain family has been separately amplified by appropriate primer pairs in order to compensate specific PCR efficiency according to primers annealing temperature.

The unique $V_\kappa C_\kappa$ repertoire thus obtained was not a naive repertoire, since the patients had been previously exposed to over-expression of the folate receptor alpha antigen. It potentially contained genes for antibodies developed against the specific tumour and possibly against the alpha folate receptor expressed in women with such disease.

The library thus obtained was used to select a new light chain compatible with the C4 heavy one. Since the inventors were looking for an antibody fragment sharing the same specificity for the alpha folate receptor as the C4 molecule, a guided selection protocol was applied. After three runs of panning on ovarian carcinoma cells (OVCAR-3 cells), using the C4 heavy chain as guiding template to select a new kappa light chain, several phages were picked up randomly and assessed for their binding capacity on these cells. The best binder was identified and named AFRA (Anti Folate Receptor Alpha).and its light chain sequenced.

The selected kappa light chain amino acid sequence is reported in FIG. 1. AFRA and the C4 fragment have the same heavy chain, with the exception of a Q1N mutation introduced at the first amino acid of the AFRA heavy chain, as reported in Example 1c.

b) Expression of Fab in E. coli:

Expression constructs suitable for expression of the AFRA Fab fragment and the C4 Fab fragment in E. coli were then prepared: the genes coding for the heavy and light chains of AFRA or C4 were cloned in frame with leader sequences (StII leader derived from E. coli heat stable enterotoxin II) in order to address the fragment synthesis to the Escherichia coli periplasmic compartment. The expression vector was specially designed for fermentation, containing a bicistronic construct encoding both the light and heavy chains under the control of the arabinose araP promoter together with a pyrC selectable marker encoding dihydroorotase (the basic expression cassette is described in European patent application EP 05109274.0 filed in the name of Dompé S.p.a. on 6 Oct. 2005, incorporated herein by reference, and in WO 2007/039632). The bicistronic vector was designed to express a faint excess of the first (light) chain, compared to the expression of the second (heavy) chain because in the present case, the heavy chain, when expressed alone can be toxic for Escherichia coli.

The vector expressing AFRA is designated DoB0134 (see FIG. 2), and has been deposited at the CNCM (Collection Nationale de Cultures de Microorganismes, Institut Pasteur, 25 Rue du Docteur Roux, F-75724 Paris Cedex 15, the 15 Mar. 2006, in the Escherichia coli strain BW25113 PyrC:: Kan (lacl$^q$, rrnB$_{T14}$, ΔlacZ$_{WJ16}$, hsdR514, ΔaraBA-D$_{AH33}$, ΔrhaBAD$_{LD78}$)) under accession number CNCM I-3586. This strain expresses the AFRA light chain with the N-terminal modification described in Example 1c, and a heavy chain including the natural hinge region.

The expression vector DoB0134 was transformed into Escherichia coli and the AFRA antibody fragment was expressed and purified. For comparative purposes, analogous experiments were carried out using the corresponding construct expressing the known C4 Fab.

During the production of C4, significant accumulation of homo light chain dimer ($L_2$) was observed, representing up to 50% of the recombinant protein synthesis. This may be partially due to the design of the expression vector which expresses a slight excess of the first chain, compared to the expression of the second chain. However, this expression vector has been used to produce several different Fabs and no homodimer light chain production has ever been observed with other sequences. This $L_2$ homodimer is a useless microorganism by-product which represents a considerable disadvantage in the production process. Indeed, it weighs heavily on the host metabolism, is difficult to separate from the useful Fab', does not have any target binding capacity and is produced in place of the desired fragment.

On the contrary, the AFRA Fab of the invention does not produce any detectable homodimer light chain from the same expression vector and from the same Escherichia coli strain. Therefore, the overall production yield is artificially increased and the chromatographic column capacities are strongly reduced since there is no competition for resin binding between the Fab' fragment of interest and the homo light chain dimer.

The specificity of the AFRA Fab was assessed using FACS. Fluorescence shift was registered only with cells expressing the human alpha folate receptor.

c) Modification of the N-Terminus Q1N Mutation AFRA:

As a result of the initial guided selection protocol using the C4 heavy chain as guiding template, AFRA and the C4 fragment originally had the same heavy chain, the first amino acid of which was a glutamine. However, it is known that glutamine in this position may be subject to conversion into a pyroglutamic acid[19] which generates product heterogeneity. N-terminal glutamine was therefore substituted with asparagine using site directed mutagenesis. Such replacement reduces the amino acid side chain length by one carbon, preventing its cyclisation. A site directed mutagenesis was performed to modify the DNA triplet codon corresponding to the first amino acid of the AFRA heavy chain and turn it into the desired asparagine residue.

The site directed mutation was confirmed by sequencing the whole gene to verify that, with the exception of this mutation, no other unexpected mutations had been inserted during the PCR amplification. The corresponding protein was produced and purified to homogeneity. This time reverse phase HPLC analysis on a di-Phenyl column revealed a single peak at any pH corresponding to a unique species. This was confirmed by electrospray mass analysis where the AFRA molecular weight was in agreement with the one calculated from its primary structure.

2. Binding Characteristics of the AFRA Fab Fragment to the Human Folate Receptor Alpha:

The new AFRA human Fab fragment was assessed for its capacity to bind the human folate receptor alpha and its binding was compared to C4 binding. The kinetic analysis was performed by plasmon resonance with BIAcore equipment (Pharmacia) using soluble recombinant human alpha folate receptor as the target protein (see FIG. 8).

a) Purification of Soluble Alpha Isoform of the Folate Receptor (αFR)

A Chinese-Hamster ovary (CHO-K1) cell line expressing the alpha isoform of the Folate Receptor (αFR) was constructed. To facilitate the purification, the soluble αFR gene was subcloned into pIRESneo expression vector to express the soluble His-Tagged alpha isoform of the folate receptor glycoprotein. In order to generate a soluble protein and by PCR technique utilizing opportune primer pairs, a shortened form of αFR, terminating at amino acid position 234, was engineered to eliminate the carboxiterminal portion of the receptor which mediated the anchor of the protein to plasmatic membrane (GPI-anchor).

The PCR primers were designed to posses the restriction site, half EcoRV in forward primer and EcoRI in the reverse primer, which are compatible with pIRES-neo vector multiple-cloning restriction sites. The PCR products were purified using Quiaex gel Extraction Kit (Quiagen) and digested with EcoRI. After digestion products were purified and ligated overnight to EcoRI and EcoRV digested and dephosphorylated pIRES-neo vector using the T4 ligation system (Biolabs). The ligated samples were transformed into *Escherichia coli* DH5_ and plated onto the LB-agar Ampicilin plates.

Several amp$^R$ colonies were picked and checked using PCR technique. One clone which showed the right pattern was selected for DNA extraction and expression studies. The DNA sequence of the expression vector was confirmed using automatic sequencing.

The expression vector was then transfected into CHO cells and stable clones were selected through neomycin resistance. Among them the best producing clone was confirmed by western blot analysis of culture supernatant and production was scaled up to 1 liter. The culture supernatant was clarified by centrifugation at 10000×g for 15 min to separate the supernatant from the cells and filtered at 0.22 μm and purification was carried out at 4° C. while all buffers contained Tween-20 0.05%.

The folate receptor protein was purified from the supernatant as follows. In the first step, the His-tagged glycoprotein was concentrated with immobilized metal affinity chromatography (IMAC) using Ni$^{++}$-Charged Chelating Sepharose Fast Flow (Amersham Biosciences, Uppsala, Sweden) as described. The CHO cell culture supernatant was applied to the column pre-equilibrated with 20 mM Phosphate, 0.15 M NaCl pH 7.0 at the flow rate of 5 ml/min. After all the supernatant was applied to the column, which was washed with the starting buffer until the $A_{280nm}$ in the eluent was back at the baseline. The protein was eluted with the same buffer containing 0.5 M of Imidazole. The $A_{280\,nm}$ peak was collected for the next step. At this point, the endogenous folate molecule were dissociates from the αFR by lowering the pH to 3.0 by the drop-wise addition of 1 M HCl and stirred in a ice-bath for 1 h. Next the sample was subjected to buffer exchange on a G-25 Sephadex column (HiPrep 26/10 desalting Amersham Biosciences, Uppsala, Sweden) with 20 mM Phosphate, 0.15 M NaCl pH 7.0. Finally, the sample was passed slowly (0.5 ml/min) through a 2 ml column of folic acid-Sepharose (Sigma Chemical Co., St. Louis, Mo.) equilibrated with 5 CV of 20 mM Phosphate, 0.15 M NaCl pH 7.0. The flow-through was collected for analysis. After column washing with the equilibration buffer, the αFR was eluted from the affinity resin with 0.1 M glycine 0.5 M NaCl pH 2.8.

Fractions were collected in polypropylene test tube containing 50 ml of 1 M sodium phosphate pH 7.0 to raise the pH of the effluent to 7.0. The purity of the αFR in this preparation was determined by SDS (15%) polyacrylamide gel electrophoresis (PAGE) under non-reducing conditions according to the method of Laemmli (13) and the gel was stained for protein with Coomassie brilliant blue. Fractions appearing 100% pure were pooled and subjected to a determination of protein concentration using DC Protein Assay kit (Bio-Rad Richmond, Calif.) using BSA as standard (14). Purified FR was stored at −25° C. in small aliquots.

b) Affinity Measurement

The target protein was coated on C5 BIAcore sensorchip and several concentrations of both antibody fragments were used to determine the binding kinetics. In particular, recombinant FR was covalently bound to a CM5 sensor chip using the amine coupling kit (Pharmacia) with an antigen concentration of 0.6 μg/ml in 10 mM sodium acetate, pH 4.8 yielding a surface of 280 RU. Residual activated groups were blocked by injection of 35 I ethanolamine (1.0 M pH 8.5). The apparent kinetic dissociation rate constants ($K_{off}$) were calculated under saturating conditions of antibody from 200 nM to 3.125 nM, with a buffer flow rates of 50 μl/min using wizard program. Evaluation was performed for at least 30 minutes. Subsequently, detachment of residual antibody bound to the sensor chip was performed with 100 mM Glycine Buffer pH 2.7.

Figure 3:
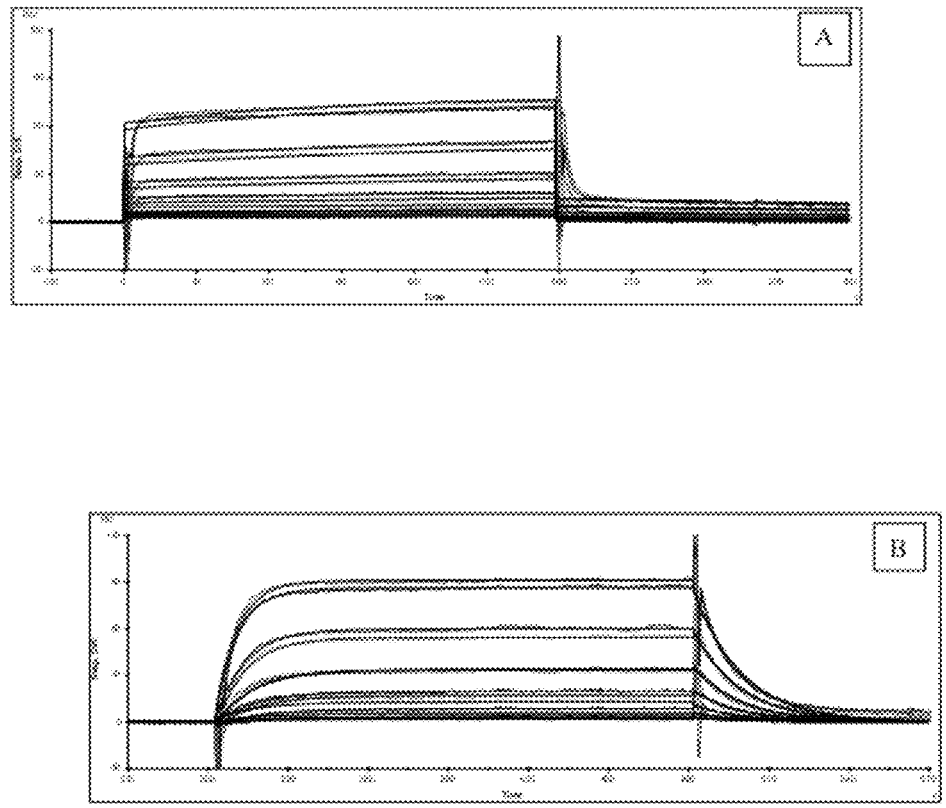

The respective affinities were deduced from the binding curves. Both C4 and AFRA were able to bind the immobilized antigen. However, the calculated $K_D$ (43.9 nM) of AFRA was more than 3 times lower than that of C4 (168 nM), indicating a higher affinity. Results are reported in FIG. 3. The binding kinetic s of AFRA monomer shows a very high association rate but also an elevated dissociation constant, which can sometimes be a disadvantage for an antibody committed to radioimmunotherapy, since, once the antibody is bound to the tumour, its long lasting effect is essential for efficient tumour irradiation.

3. Production of Natural Dimer F(ab')2 and in vitro Binding Characteristics of F(ab')2:

a) Natural Dimerisation

To slow down the dissociation rate of the AFRA Fab, and to further increase the fragment avidity it was decided to dimerize the Fab fragment. To do so, the penta peptide DKTSC, corresponding to the natural hinge sequence of the Gamma 1 human family, was added to the carboxy terminus of both AFRA and C4 heavy chains, giving rise to a fragment designated Fab' (i.e. Fab with an extra free cysteine on the carboxy terminal, belonging to the hinge region). From this Fab' format it was then possible to obtain an F(ab')$_2$ dimer by the natural oxidation of the free cysteine residue purposely added at the carboxy terminus of the antibody heavy chain[20] and corresponding to the first cysteine of the natural full length antibody hinge region.

Both AFRA and C4 fragments were incubated with TCEP (Tris(2-carboxyethyl)phosphine hydrochloride) in mild conditions to reduce the carboxy terminus heavy chain cysteine, buffer was exchanged to remove the reducing agent and pH adjusted to 8, where disulfide bond formation is known to be chemically favoured.

Figure 4:
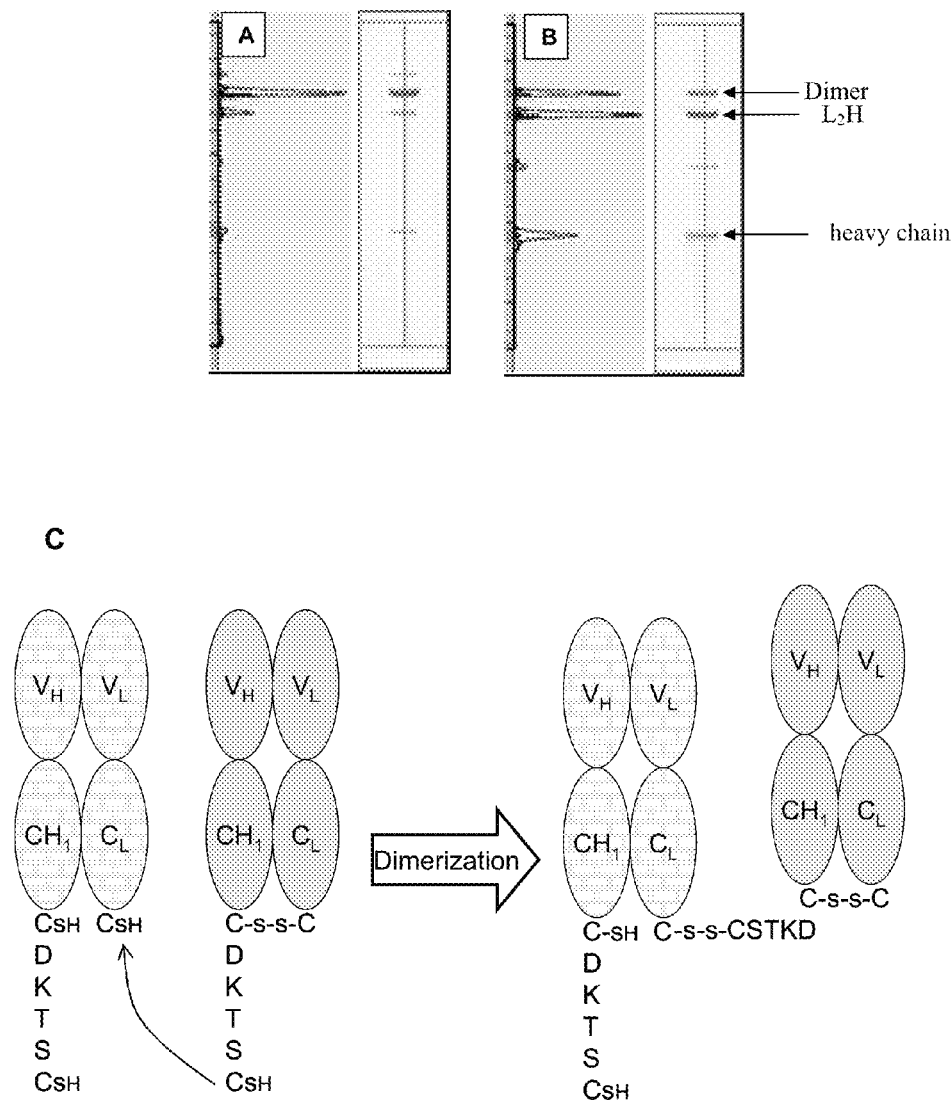

Dimers were separated from the reaction mixture by gel filtration chromatography where they were resolved as a unique peak. SDS-PAGE analysis revealed that dimer preparations were not as homogenous as one would have expected and peaks originated several bands on the gel:

For the AFRA fragment, the major band, representing 80% of the material, migrated as expected in the range of 100 kDa and was assigned to the AFRA dimer. Another band, representing 16% of the whole material, with an apparent molecular weigh of 75 kDa could be detected and was attributed to a "dimer" composed of a normal monomer covalently linked to another Fab light chain ($L_2H$). This "dimer" resulted from the unusual attack of the carboxy terminal cysteine from the first monomer on the carboxy terminal cysteine of the light chain of a second Fab monomer. This light chain cysteine is the one normally involved in the disulfide bond with the heavy chain and therefore cannot be available for any other disulfide bond formation. Since in the resulting dimer the Fab heavy chain is no more covalently bound to the rest of the molecule, and only interacts through Van der Waals and hydrophobic interactions with the light chain, this entity elutes as a normal dimer during gel filtration purification which is run in native conditions, but is resolved as two bands during SDS-PAGE analysis where the detergent (SDS) concentration is sufficient to break down the molecule (FIG. 4). In effect in this lane, together with the $L_2H$, another band corresponding to the non-covalently bound heavy chain snatched from the dimer surrogate can be detected at the bottom of the gel and represents 4% of the overall material.

In the case of the C4 Fab, the situation was surprisingly even worse since this time in SDS-PAGE the major band (43% of the entire material) corresponded to the $L_2H$ compound or, in other words, the impurity of the AFRA reaction had now become the most abundant product of the C4 dimerization reaction. The covalently linked dimer represented only 29% of the whole material and the SDS separated heavy chain 25% of the mixture. This analysis was further confirmed by LC-mass investigation which was able to unequivocally identify all the species present in the material obtain after gel filtration purification.

In native aqueous conditions no differences in chromatographic behaviour between the correct dimer and the impurity, corresponding to the "dimer" with the heavy chain not covalently linked, can be used to separate the two species. The inventors unsuccessfully tried to separate both species by ion exchange or hydrophobic interactions chromatography to attempt to obtain a pure dimer. The inventors also tried without success to eliminate the impurity from the dimer by selective heat denaturation.

b) ELISA: Alpha Folate Receptor Direct Binding of F(ab')2

The two $F(ab')_2$ dimers were then tested for binding, in an ELISA format, directly on an A431 cell line transfected with the human alpha folate receptor, and on human ovarian carcinoma lines OVCAR3 and IGROVI cells.

$4 \times 10^4$ cells (human ovarian carcinoma cell lines OVCAR3 (ATCC) and IGROVI (a gift from Dr J. Bénard, Institut Gustave Roussy, Villejuif, France), and A431-FR[17] cells which are human epidermoid carcinoma cells transfected with folate receptor alpha,) were seeded in each well of a 96 wells format plate, and grown until a confluent monolayer was obtained. Cells were fixed, for 5 minutes, at room temperature with 0.1% glutaraldehyde in PBS. Plates were washed twice with PBS, then once (5 minutes) with 0.1M glycine in PBS+0.02% $NaN_3$, successively five times with PBS and finely with PBS containing 1% BSA and 0.02% $NaN_3$.

Serial dilutions of antibody fragments (C4 or AFRA) were allowed to bind for 1 hour at room temperature in PBS+0.03% BSA and washed three times with PBS.

An anti-human IgG (Fab specific, Sigma) peroxidase conjugated diluted 1:1000 in PBS+0.03% BSA was used to reveal antibodies fragment binding. The ELISA plate was revealed with addition of 100 µl of TMB solution (Sigma) for 30 minutes at room temperature, stopped by addition of 50 µl of $H_2SO_4$ solution (1M) and read at 450 nm.

Since no signal could be detected on the A431 mock cells which are cells transfected with the empty vector, as compared to the cells transfected with FR-alpha, both AFRA and C4 antibodies were judged to be specific for the alpha folate receptor. Both fragments showed almost the same overall affinities in the low nanomolar range, potencies compatible with a radioimmunotherapy use (note however that the C4 $F(ab')_2$ is so highly contaminated with the pseudo dimer $L_2H$ that its practical uses, particularly in radioimmunotherapy, is not feasible). Table I reports ELISA determination of $K_D$ values of $F(ab')_2$ of C4 and AFRA antibodies fragments. The $K_D$ was determined as to be the concentration at which half of the ELISA plateau signal is obtained.

TABLE I

| $F(ab')_2$ | $K_D$ (nM) | | |
|---|---|---|---|
| | OVCAR3 | A431-FR | IGROV1 |
| C4 | 11 ± 2 | 1.2 ± 0.1 | 118 ± 64 |
| AFRA | 26 ± 10 | 2.5 ± 0.7 | 57 ± 21 |

Chemical Dimerisation of Fab' and in vivo Binding Characteristics:

In vivo assays are performed in order to verify tumour specificity and localization. However, in vivo, the disulfide bridge maintaining together the two halves of the $F(ab')_2$ molecule is rapidly hydrolysed and the $F(ab')_2$ is quickly reconverted into a Fab fragment and cleared from the blood stream. Chemical dimerisation, as described below, is therefore carried out to maintain the $F(ab')_2$ format in vivo.

a) Dimerization of Fab' Fragment with Bismaleimide (BMOE)

In order to conserve the $F(ab')_2$ format in vivo, a non hydrolysable linker connecting the two Fab' forming the $F(ab')_2$ was used[21]. More specifically, a bismaleimide ethane linker (BMOE) was identified in order to dimerize the Fab' fragment[22] into a Di Fab Maleimide (DFM). Both AFRA and C4 Fab fragments were subject to this treatment and tested in an in vivo biodistribution experiment, so as to identify the best candidate for clinical development.

Chemical dimerization of Fab' into DFM has already been reported in the literature. This chemical reaction is based on the unique capacity of cysteine residues to specifically react with maleimide heterocycle. The chemical reaction leads to the formation of a chemical bond between cysteine residues and the maleimide. In the present case, the unique free cysteine on the Fab' protein was at the carboxy terminus of the Fab' heavy chain. Therefore the maleimide attack was site specific and on the opposite side of the folate receptor binding site.

The protein was incubated with 70 mole of TCEP (Tris(2-carboxyethyl)phosphine hydrochloride) per mole of Fab' for 5 hours at room temperature to reduce the heavy chain carboxy terminal cysteine residue. TCEP was removed by HiPrep Desalting chromatography 26/10 (General Electrics) previously equilibrated in MES 40 mM pH 6.0. Protein was concentrated down to 8 mg/ml and incubated with gentle stirring at RT for 2.5 hours to allow the disulfide bond present in-between the Fab chains to reoxidize. The reaction kinetics was monitored by RP-HPLC analysis. BMOE linker (Sigma) was added to the protein solution (1 mg/ml in DMSO) in a molar ratio of 0.35 linker/protein and incubate for 16 hours at room temperature with gentle stirring.

In order to remove natural F(ab')$_2$ the reaction mixture was again reduced with 70 mole of TCEP per mole of Fab' for 3.5 hours at room temperature. Dimer was purified on HiPrep Sephacryl S-100 HR column, previously equilibrated with MES 40 mM pH 6.0. Protein was SDS-PAGE analysed and quantified by Bradford.

With this strategy AFRA-DFM was obtained with almost the same amount of L$_2$H impurity. Surprisingly, however, it was practically impossible to obtain any correct C4-DFM. It was estimated, by gel filtration after disulfide reduction to get rid of the "natural" dimer, that only 4% of the C4 molecules reacts with the linker to form the DFM. The protocol was repeated several times with the C4 Fab' and different conditions were used but the inventors never succeeded in obtaining higher dimer concentrations. The reaction was followed step by step by mass analysis and it was shown that the reaction did not proceed after addition of a BMOE molecule on the Fab'. The linker was probably reacting in an unexpected way, probably due to the lambda light chain of C4 which constitutes the only difference between the AFRA and C4 Fab fragments. By way of contrast, in the same conditions dimerization was always observed for the AFRA moiety (TABLE II).

TABLE II

| Antibody fragment | Overall % dimerization | High MW | Dimer L$_2$H$_2$ | L$_2$H | 60 kDa | Fab' | H free chain |
|---|---|---|---|---|---|---|---|
| F(ab')$_2$-C4 | 65 | — | 29 | 43 | — | — | 25 |
| F(ab')$_2$-AFRA | 61 | — | 80 | 16 | — | — | 4 |
| DFM-C4 | 4 | 3 | 34 | 17 | 17 | 14 | 15 |
| DFM-AFRA | 44 | 10 | 48 | 17 | — | 17 | 8 |

From this table it can be seen that with C4 an unexpected product can be characterized at 60 kDa, but that the rest of the dimerization reaction leads to almost the same products in the same quantities. A significant difference can be seen between AFRA and C4 with respect to the % of dimer obtained at the end of the reaction with more than a factor 10 between the two molecules in favor of AFRA.

b) Immunohistochemistry Assay on Biopsy Samples

The assays reported above were performed in vitro on transfected cells or ovarian carcinoma cell lines. However the different cell lines may each express different quantities and different glycosylation variants of the receptor. Therefore, it is important to test the Fab dimers in an in vivo context. AFRA was tested in an immunohistochemistry assay for its capacity to recognize in situ the alpha folate receptor expressed from an ovarian carcinoma.

The AFRA-DFM dimer was FITC labelled in vitro, and biopsy samples were prepared for staining. Specifically, frozen sections of biopsy samples, 5 mm thick, were cut, dried and fixed in cold acetone for 5 min. Acetone excess was eliminated by washing slides in PBS (pH 7.4) and then air drying. The cryostat sections were blocked with 3% BSA, 10% human sera in 3% skimmed milk for 60 minutes at room temperature. The FITC DFM-AFRA labelled antibody fragment was primary incubated, overnight at 4° C., at three different dilutions.

Autostainer buffer wash was performed. An anti-FITC mAb (rabbit dilution 1:200) was added for 30 minutes at room temperature. The slides were successively washed with an autostainer buffer. Then a swine anti-Rabbit Ig, Alkaline Phosphatase conjugated, mAb was added (dilution 1:80) for 30 minutes at room temperature. Slides were washed with an autostainer buffer. Successively, Red Buffer (provided by Vector) was added, washed, and the last wash was done in distilled water. Haematoxylin was added, for 15 seconds at room temperature. Slides were washed in tap water, dehydrated, cleared and mounted for microscope observation.

Figure 5:
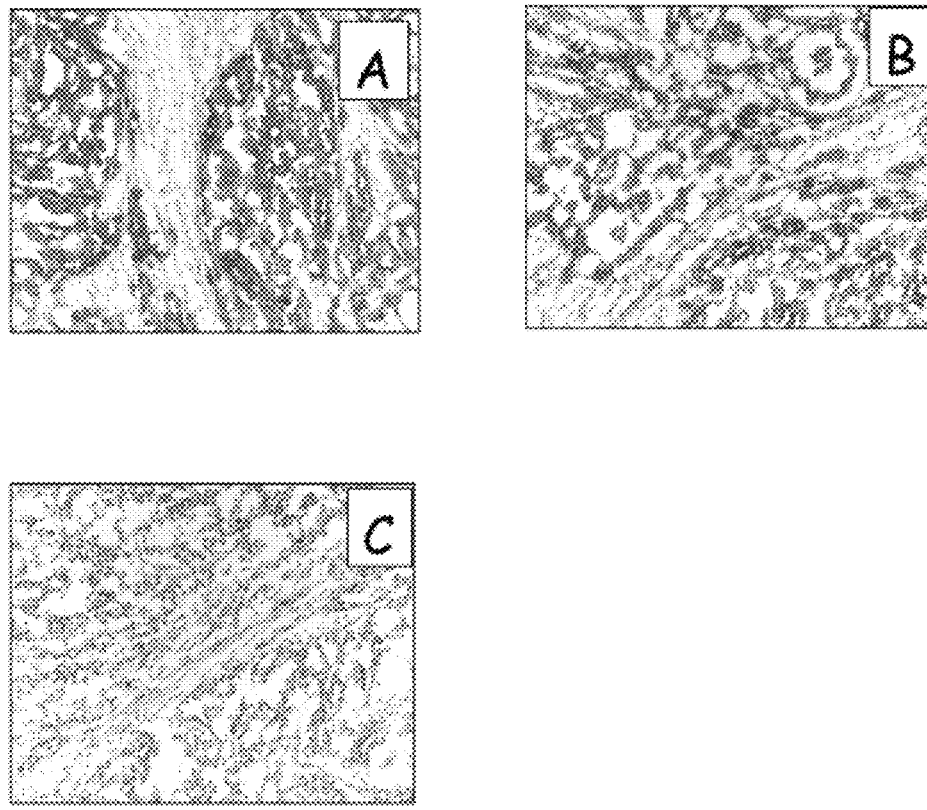

AFRA-DFM was again able to localize into the tumour area and did not stain any surrounding healthy tissues (FIG. 5), confirming the specificity of the AFRA-DFM dimer in an in vivo context.

c) Biodistribution in vivo

Having demonstrated the AFRA-DFM specificity, a biodistribution experiment was carried out. To this aim the macromolecule was radiolabeled with iodine$^{131}$ by the Iodogen pre-coated iodination tubes using Chizzonite method, essentially as described by manufacturer (Pierce) using pyrogen-free clinical grade reagents[17]. The Chizzonite method enables to better preserve the integrity and functionally of the molecule; in fact, the final radiolabeled product, at a specific activity of 5 mCi/mg, showed a mean immunoreactivity of at least 65%. The $^{131}$I-labeled AFRA-DFM was injected into animal blood.

At several predetermined post injection times animals were sacrificed, organs were isolated, weighed and counted to determine the kinetics of radioactivity accumulation and elimination in each of them. Normal tissues were used as references versus the tumour which had been previously implanted under the animal skin.

More specifically, female CD1 nu/nu mice (athymic) were obtained at 5-6 weeks of age from Charles River Laboratories (Calco, Italy). After 1 week of acclimatization, mice were xenografted subcutaneously with 3.5×10$^6$ A431 cells transfected with human folate receptor alpha or A431tMock cells in 0.1 mL of 0.9% NaCl. Two to three weeks after tumour cell injection, mice were randomly divided into groups and injected intravenously in the lateral tail vein with the radiolabeled antibody fragment ($^{131}$I-DFM-AFRA 5.3). The experiment was performed with this radioisotope and details are reported in Table III below:

TABLE III

| | |
|---|---|
| Xenographed tumour examined | A431FR |
| Group size per time | 4 |
| Specific activity (mCi/mg) | 5.0 |
| Total injected dose (μCi)/animal | 30.0 |
| Total injected dose (μg)/animal | 6.0 |
| Evaluated time points a.i. for Biodistribution (h) | 1, 3, 6, 15, 24, 48 |
| Evaluated time points a.i. for Pharmacokinetics (h) | 10 min, 30 min, 1, 3, 6, 15, 24, 48 | d) Radio-localization

After dissection, tumours and other tissue/organs (spleen, kidney, liver, bladder with urine, sternum, heart and muscle) were collected and wet-weighted. Radioactivity associated with each tissue was assessed with a gamma counter with internal standards (5 and 10 µl of the injected solution).

Figure 6:
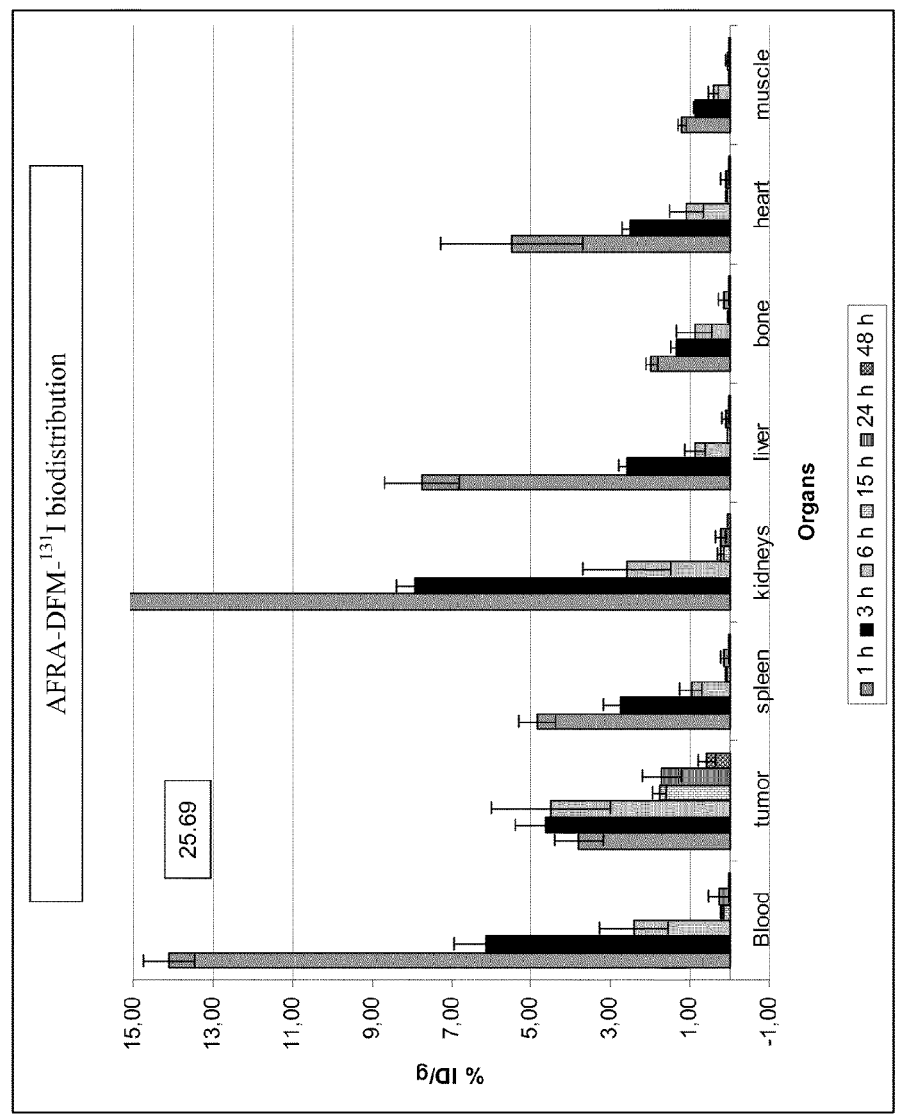

Results are presented in FIG. 6 and are expressed as the percentage of the injected dose per gram of tissue (% ID/g) and are compensated for radioactivity decay. In this way normalization allows the direct comparison of organs or animals. For radioimmunotherapy the ideal molecule will have a high accumulation with a long lasting time in the tumour and the lowest possible background in healthy tissues.

The result of this biodistribution experiment demonstrates that AFRA-DFM specifically accumulates in the tumour. Elevated values corresponding to bladder and urine correlates well with the expected DFM excretion and validate the detoxification pathway. As expected, DFM accumulates in the tumour where, six hours post injection, its concentration started to be superior to the concentration measured in other organs.

5. Proof of Principle of the in vivo Efficacy of Radiolabeled AFRA-DFM

Having demonstrated that the radiolabeled antibody fragment $^{131}$I-DFM-AFRA specifically accumulated in the tumour ectopically expressing FR (A431FR), its ability to control tumour growth was assessed. The total injected dose was defined according to the pharmacokinetics. The macromolecule was radiolabelled with iodine$^{131}$ and injected into the blood stream in animals bearing subcutaneously implanted tumor cells.

More specifically, female CD1 nu/nu mice (athymic) were obtained at 7 weeks of age from Charles River Laboratories (Calco, Italy). After 1 week of acclimatization, mice were xenografted subcutaneously with $3.5 \times 10^6$ A431 cells transfected with human folate receptor alpha (A431FR) or A431tMock cells in 0.1 mL of 0.9% NaCl (saline). One week after tumour cell injection, mice were randomly divided into groups and injected intravenously in the lateral tail vein with 0.3 mL of the radiolabelled AFRA-DFM in saline or saline alone as control. The tumor growth was monitored every 2-3 days and measured by calliper; the tumor volume was determined as follows: $D \times d^2 \times \frac{1}{6} \times \pi$ where D=major diameter, d=minor diameter. Three independent experiments were performed and details are reported in Table IV below:

TABLE IV

| Xenographed tumour examined | A431FR and A431mock |
|---|---|
| Number of independent experiments | 3 |
| Group size per treatment | 6-7 |
| Mean specific activity (mCi/mg) | 4.87 ± 0.57 |
| Total injected radioactive dose (µCi)/animal | 1002 ± 80 |
| Total injected protein (µg)/animal | 211 ± 35 |

Figure 11:
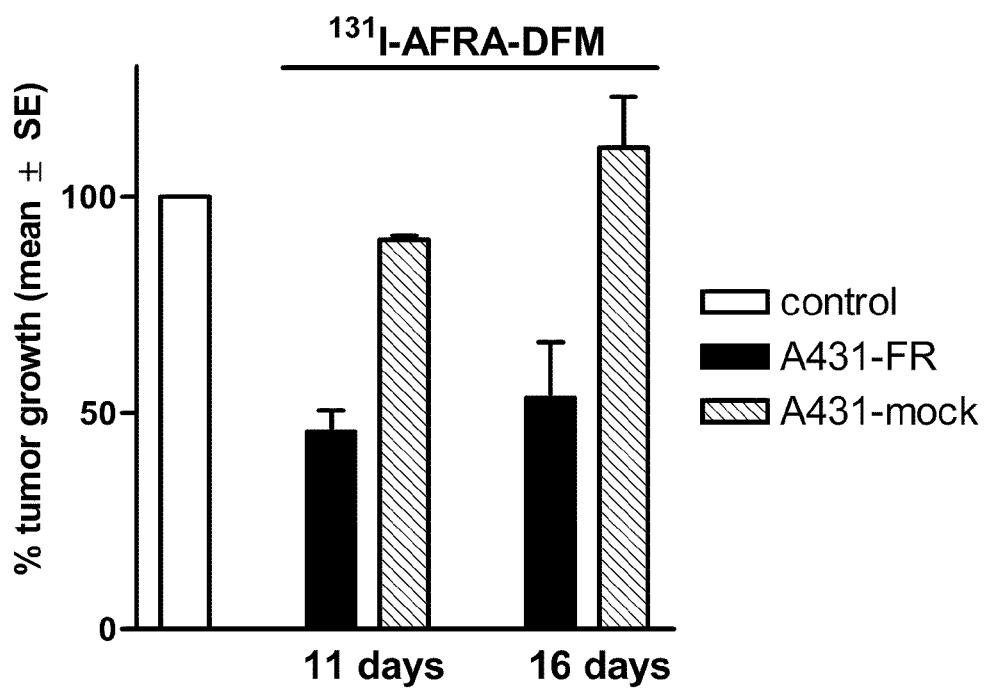

Results are presented in FIG. 11 and are expressed as the percentage of tumor growth relative to the control treated with saline alone. The AFRA-DFM radiolabelled with $^{131}$I was injected in tumour bearing mice at an average dose of 1 mCi/mouse. Tumor growth was monitored every 2-3 post injection. The results of tumor growth delay, recorded in three independent experiments, are reported in FIG. 11 as the mean percentage of tumor growth relative to the respective control. In each experiment the mean volume in each treated group, i.e. A431FR or A431mock, was compared with the mean volume of the respective control group. The results of these efficacy experiments demonstrate that radiolabelled AFRA-DFM specifically delayed the growth of tumors expressing the target antigen of interest (A431FR) but not of irrelevant tumors (A431mock) and that the percent of tumor reduction was significant at both 11 and 16 days after treatment (p=0.006 and p=0.05 respectively).

6. Localization of Radiolabeled AFRA-DFM on Ovary Carcinoma Cells Growing as i.p. Tumors Having demonstrated that the radiolabelled antibody fragment $^{131}$I-DFM-AFRA, after i.v. injection, was able to specifically accumulate in and control growth of the tumour ectopically expressing FR (A431FR) its ability to localize on ovarian carcinoma cells, naturally overexpressing the folate receptor, was assessed. $^{131}$I-DFM-AFRA was injected into the peritoneal cavity in animals bearing intraperitoneally implanted ovarian carcinoma cells, a model that mimics the natural growth and dissemination of human epithelial ovarian cancer.

More specifically, female CD1 nu/nu mice (athymic) were obtained at 7 weeks of age from Charles River Laboratories (Calco, Italy). After 1 week of acclimatization, mice were xenografted intraperitoneally with $8\text{-}10 \times 10^6$ IGROV1 cells, overexpressing human folate receptor alpha, in 0.3 mL of 0.9% NaCl (saline). When ascite formation becomes evident (14-20 days after tumour cell injection) radiolabelled AFRA-DFM was administered intraperitoneally in 0.3 mL of saline, mice randomly divided into groups and at different time-points ascite, solid tumour masses, growing adherent to the peritoneum, and other tissue/organs (blood, kidneys, liver, and muscle) were collected and wet-weighted. Ascite was centrifuged, pelleted ascitic tumor cells were separated from fluid and counted separately. Radioactivity associated with each tissue was assessed with a gamma counter with internal standards (5 and 10 µl of the injected solution). Three independent experiments were performed and details are reported in Table V below:

TABLE V

| Xenographed tumour examined | IGROV1 |
|---|---|
| Number of independent experiments | 3 |
| Group size per time | 3-4 |
| Range specific activity (mCi/mg) | 3.9-9.7 |
| Total injected radioactive dose µCi/animal (range) | 30-158 |
| Total injected protein µg/animal (range) | 3.6-40 |
| Evaluated time points for Biodistribution (h) | 1, 3, 6, 15, 24 |

Figure 12:
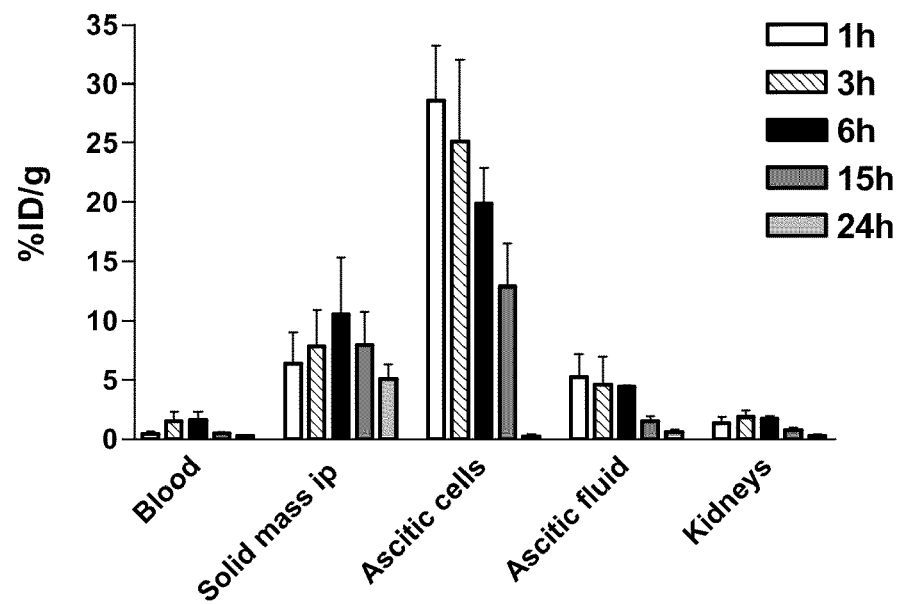

Results are presented in FIG. 12 and are expressed as the percentage of the injected dose per gram of tissue (% ID/g) and are compensated for radioactivity decay. In this way normalization allows the direct comparison of organs or animals. The results of these experiments demonstrate that radiolabelled AFRA-DFM specifically bound to the surface of ovarian cancer cells present in the ascite (IGROV1) and that radiolabelled AFRA-DFM persisted on the cell surface and solid tumour masses for up to 15 h.

7. Efficacy of Radiolabeled AFRA-DFM Against Ovary Carcinoma Cells Growing as i.p. Tumors Having demonstrated that $^{131}$I-DFM-AFRA was able to specifically accumulate in tumour naturally expressing FR (IGROV1) after i.p. administration, its ability to control intraperitoneal tumour dissemination of ovarian carcinoma was assessed. $^{131}$I-DFM-AFRA was injected into the peritoneal cavity in animals bearing intraperitoneal ovarian carcinoma cells implanted 2-4 days before antibody fragment administration.

More specifically, female CD1 nu/nu mice (athymic) were obtained at 7 weeks of age from Charles River Laboratories (Calco, Italy). After 1 week of acclimatization, mice were xenografted intraperitoneally with $8\text{-}10 \times 10^6$ ovarian carcinoma cells, overexpressing human folate receptor alpha, (IGROV1 or OVCAR3) in 0.3 mL of 0.9% NaCl (saline). Two or four days after tumour cell injection mice were randomly divided into groups and injected intraperitoneally vein with 0.3 mL of the radiolabelled AFRA-DFM in saline or saline alone as control. The tumour growth was monitored every 2-3 days, weighted and monitored for ascite formation or solid i.p. mass development. The animal survival was recorded. Two independent experiments were performed and details are reported in Table VI below:

TABLE VI

| Xenographed tumour examined | IGROV1 or OVCAR3 |
|---|---|
| Number of independent experiments | 2 |
| Group size per treatment | 8-9 |
| Mean specific activity (mCi/mg) | 4.3 |
| Total injected radioactive dose (µCi)/animal | 1.004 |
| Total injected protein (µg)/animal | 250 |

Figure 13:
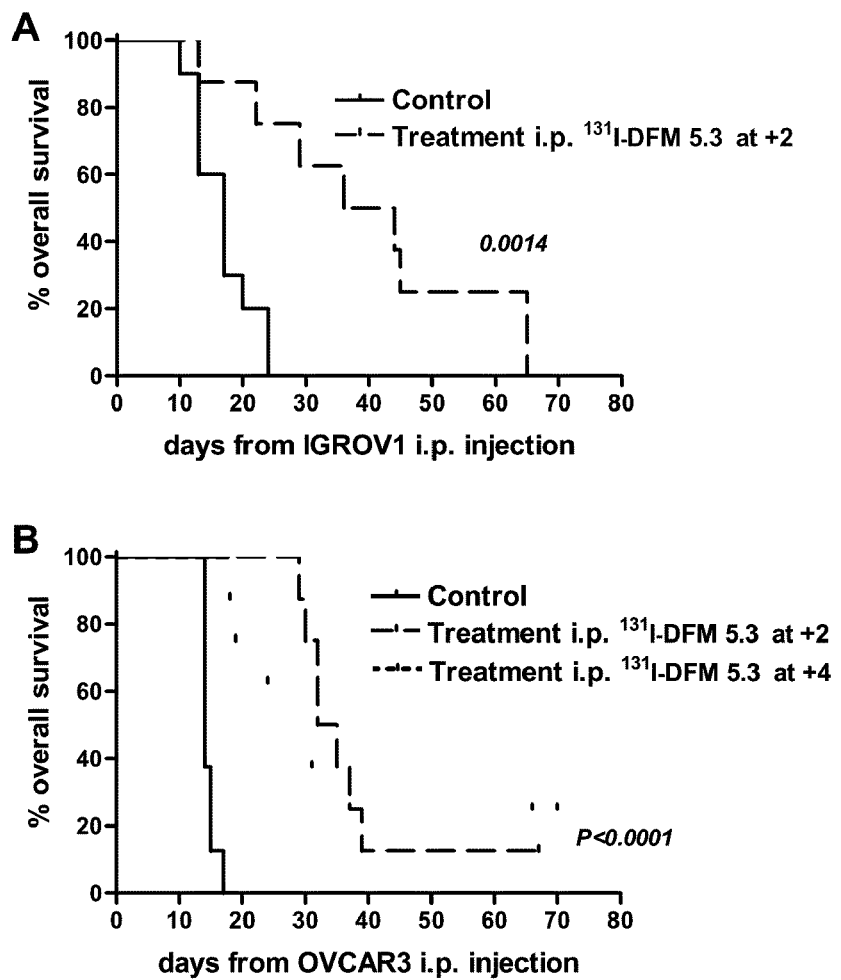

Results are presented in FIG. 13 and are expressed as survival curves. The increase in survival was evaluated by log-rank assay. The results of these experiments demonstrate that radiolabelled AFRA-DFM, when injected up to 4 days after tumour implantation on the peritoneal cavity, was able to significantly delay the tumour growth and accordingly to prolong animal survival in both orthotopic tumour models ($p=0.0014$ and $p<0001$ in IGROV1 and OVCAR3 model respectively).

BIBLIOGRAPHY

[1] Jemal A, Murray T, Ward E, et al. Cancer statistics, 2005. CA Cancer J Clin 2005; 55:10-30.

[2] Cannistra S A. Cancer of the ovary. N Engl J Med 2004; 351:2519-29.

[3] Harries M, Gore M. Part I: chemotherapy for epithelial ovarian cancer-treatment at first diagnosis. Lancet Oncol 2002; 3:529-36.

[4] Vasey P A. Resistance to chemotherapy in advanced ovarian cancer: mechanisms and current strategies. Br J Cancer 2003; 89 Suppl 3:S23-S28.

[5] Bast R C Jr, Klug T L, St John E, Jenison E, Niloff J M, Lazarus H, Berkowitz R S, Leavitt T, Griffiths C T, Parker L, Zurawski V R Jr, Knapp R C. A radioimmunoassay using a monoclonal antibody to monitor the course of epithelial ovarian cancer. N Engl J Med. 1983 Oct. 13; 309(15):883-7.

[6] Lavin P T, Knapp R C, Malkasian G, Whitney C W, Berek J C, Bast R C Jr. CA 125 for the monitoring of ovarian carcinoma during primary therapy. Obstet Gynecol. 1987 February; 69(2):223-7.

[7] Miotti S, Canevari S, Menard S, Mezzanzanica D, Porro G, Pupa S M, Regazzoni M, Tagliabue E, Colnaghi M I. Characterization of human ovarian carcinoma-associated antigens defined by novel monoclonal antibodies with tumor-restricted specificity. Int J Cancer. 1987 Mar. 15; 39(3):297-303.

[8] Netti P A, Baxter L T, Boucher Y, Skalak R, Jain R K Time-dependent behavior of interstitial fluid pressure in solid tumors: implications for drug delivery. Cancer Res. 1995 Nov. 15; 55(22):5451-58.

[9] Jain R K. Physiological barriers to delivery of monoclonal antibodies and other macromolecules in tumors. Cancer Res. 1990 Feb. 1; 50(3 Suppl):814s-819s.

[10] Adams G P, Schier R, McCall A M, Simmons H H, Horak E M, Alpaugh R K, Marks J D, Weiner L M. High affinity restricts the localization and tumor penetration of single-chain fv antibody molecules. Cancer Res. 2001 Jun. 15; 61 (12):4750-5.

[11] Figini M et al., Cancer Res. 1998, Mar. 1; 58 (5): 991-6.

[12] King D J, Turner A, Farnsworth A P, Adair J R, Owens R J, Pedley R B, Baldock D, Proudfoot K A, Lawson A D, Beeley N R, et al Improved tumor targeting with chemically cross-linked recombinant antibody fragments. Cancer Res. 1994 Dec. 1; 54(23):6176-85.

[13] Willuda, J., Honegger, A., Waibel, R., Schubiger, P. A., Stahel, R., Zangemeister-Wittke, U., and Plückthun, A. High thermal stability is essential for tumor targeting of antibody fragments: Engineering of a humanized anti-epithelial glycoprotein-2 (epithelial cell adhesion molecule) single-chain Fv fragment. (1999) Cancer Res. 59, 5758-5767.

[14] Ewert, S., Huber, T., Honegger, A., and Plückthun, A. Biophysical properties of human antibody variable domains J. Mol. Biol. 3(2003) 5, 531-553.

[15] Tomassetti et al., J. Cellular Biochemistry, 1999 72:111-118.

[16] Stalteri M A, Mather S J. A cross-linked monoclonal antibody fragment for improved tumor targeting. Bioconjug Chem. 1995 March-April; 6(2): 179-86.

[17] Sharkey R M, McBride W J, Karacay H, Chang K, Griffiths G L, Hansen H J, Goldenberg D M. A universal pretargeting system for cancer detection and therapy using bispecific antibody. Cancer Res. 2003 Jan. 15; 63(2):354-63.

[18] Coliva A et al., Cancer Immunol. Immunotherap. 2005, December; 54 (12): 1200-13.

[19] Adamczyk M, Gebler J C, Wu J, Yu Z. Complete sequencing of anti-vancomycin Fab fragment by liquid chromatography-electrospray ion trap mass spectrometry with a combination of database searching and manual interpretation of the MS/MS spectra. J Immunol Methods. 2002 Feb. 1; 260(1-2):235-49.

[20] Humphreys D P, Vetterlein O M, Chapman A P, King D J, Antoniw P, Suitters A J, Reeks D G, Parton T A, King L M, Smith B J, Lang V, Stephens P E. F(ab')$_2$ molecules made from *Escherichia coli* produced Fab' with hinge sequences conferring increased serum survival in an animal model. J Immunol Methods. 1998 Aug. 1; 217(1-2):1-10.

[21] Casey J L, Napier M P, King D J, Pedley R B, Chaplin L C, Weir N, Skelton L, Green A J, Hope-Stone L D, Yarranton G T, Begent R H. Tumor targeting of humanised cross-linked divalent-Fab' antibody fragments: a clinical phase I/II study. Br J Cancer. 2002 May 6; 86(9):1401-10.

[22] DeSilva B S, Wilson G S. Synthesis of bifunctional antibodies for immunoassays. Methods. 2000 September; 22(1): 33-43.

The invention claimed is:

1. An isolated or purified antibody or fragment thereof, which specifically binds to folate receptor-alpha (FRa), wherein said antibody or fragment thereof is a Fab fragment comprising a light chain and a heavy chain, the light chain having a variable region ($V_L$) and a constant region ($C_L$), the heavy chain having a variable region ($V_H$) and a first constant region ($C_{H1}$), and wherein
the variable region ($V_L$) comprises the following amino acid sequences:

| | |
|---|---|
| RASESVSFLGINLIH, | (SEQ ID NO: 3) |
| QASNKDT, | (SEQ ID NO: 4) |
| LQSKNFPPYT, | (SEQ ID NO: 5) | the constant region ($C_L$) is a kappa constant region,
the variable region ($V_H$) has the amino acid sequence of SEQ ID NO: 2; and
the first constant region ($C_{H1}$) is an IgG heavy chain.

2. The antibody or fragment thereof according to claim 1, which comprises a light chain having the amino acid sequence of FIG. 1 (SEQ ID NO: 1).

3. The antibody or fragment thereof according to claim 1 which is fully human.

4. The antibody or fragment thereof according to claim 1 which is monoclonal.

5. The antibody fragment according to claim 1, which is a Fab' fragment, wherein the heavy chain further comprises a hinge region suitable for covalent bonding to a second antibody fragment.

6. The antibody or fragment thereof according to claim 1 which is conjugated to an effector moiety selected from a cytotoxic agent or a marker.

7. The antibody or fragment thereof according to claim 6 wherein the cytotoxic agent is a radionuclide.

8. The antibody or fragment thereof according to claim 7 wherein the radionuclide is selected from the group consisting of $^{131}$I, $^{90}$Y, $^{177}$Lu, $^{188}$Re and $^{99}$Tc.

9. A dimer formed by the two covalently bound Fab' fragments of claim 5.

10. A pharmaceutical composition comprising the antibody, or fragment thereof, according to claim 1, in association with a pharmaceutically acceptable carrier.

11. The pharmaceutical composition according to claim 10 wherein the antibody or fragment thereof is conjugated to an effector moiety selected from a cytotoxic agent or a marker.

12. The pharmaceutical composition according to claim 11 wherein the cytotoxic agent is a radionuclide.

13. The pharmaceutical composition according to claim 12 wherein the radionuclide is selected from $^{131}$I, $^{90}$Y, $^{177}$Lu, $^{188}$Re and $^{99}$Tc.

14. The pharmaceutical composition according to claim 11 further comprising a therapeutic agent selected from the group consisting of a chemotherapeutic agent and a radiotherapeutic agent.

15. A method for treating a disorder involving overexpression of folate receptor-alpha (FRa) which comprises administering to a subject in the need thereof an antibody or fragment thereof as defined in claim 1, wherein the disorder is ovarian carcinoma in humans.

* * * * *

SEQUENCE LISTING

<160> NUMBER OF SEQ ID NOS: 14

<210> SEQ ID NO 1
<211> LENGTH: 219
<212> TYPE: PRT
<213> ORGANISM: Homo sapiens -continued

```
<400> SEQUENCE: 1

Glu Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 120
<212> TYPE: PRT
<213> ORGANISM: Homo sapiens

<400> SEQUENCE: 2

Asn Val Gln Leu Val Glu Ser Gly Gly Gly Leu Val Gln Pro Gly Arg
1               5                   10                  15

Ser Leu Arg Leu Ser Cys Thr Thr Ser Gly Phe Thr Phe Gly Asp Tyr
            20                  25                  30

Ala Met Ile Trp Ala Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Asp Phe Trp Ser Gly Met Asp Val Trp Gly Lys
            100                 105                 110

Gly Thr Thr Val Thr Val Ser Ser
        115                 120

<210> SEQ ID NO 3
<211> LENGTH: 15
<212> TYPE: PRT
```

```
<213> ORGANISM: Homo sapiens

<400> SEQUENCE: 3

Arg Ala Ser Glu Ser Val Ser Phe Leu Gly Ile Asn Leu Ile His
1               5                   10                  15

<210> SEQ ID NO 4
<211> LENGTH: 7
<212> TYPE: PRT
<213> ORGANISM: Homo sapiens

<400> SEQUENCE: 4

Gln Ala Ser Asn Lys Asp Thr
1               5

<210> SEQ ID NO 5
<211> LENGTH: 10
<212> TYPE: PRT
<213> ORGANISM: Homo sapiens

<400> SEQUENCE: 5

Leu Gln Ser Lys Asn Phe Pro Pro Tyr Thr
1               5                   10

<210> SEQ ID NO 6
<211> LENGTH: 5
<212> TYPE: PRT
<213> ORGANISM: Homo sapiens

<400> SEQUENCE: 6

Asp Tyr Ala Met Ile
1               5

<210> SEQ ID NO 7
<211> LENGTH: 17
<212> TYPE: PRT
<213> ORGANISM: Homo sapiens

<400> SEQUENCE: 7

Ser Ile Ser Ser Ser Ser Ser Tyr Ile Tyr Tyr Ala Asp Ser Val Lys
1               5                   10                  15

Gly

<210> SEQ ID NO 8
<211> LENGTH: 11
<212> TYPE: PRT
<213> ORGANISM: Homo sapiens

<400> SEQUENCE: 8

Glu Arg Tyr Asp Phe Trp Ser Gly Met Asp Val
1               5                   10

<210> SEQ ID NO 9
<211> LENGTH: 97
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys

<210> SEQ ID NO 10
<211> LENGTH: 257
<212> TYPE: PRT
<213> ORGANISM: Homo sapiens

<400> SEQUENCE: 10

Met Ala Gln Arg Met Thr Thr Gln Leu Leu Leu Leu Leu Val Trp Val
 1               5                  10                  15

Ala Val Val Gly Glu Ala Gln Thr Arg Ile Ala Trp Ala Arg Thr Glu
                 20                  25                  30

Leu Leu Asn Val Cys Met Asn Ala Lys His His Lys Glu Lys Pro Gly
                 35                  40                  45

Pro Glu Asp Lys Leu His Glu Gln Cys Arg Pro Trp Arg Lys Asn Ala
         50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                 100                 105                 110

Leu Gly Pro Trp Ile Gln Gln Val Asp Gln Ser Trp Arg Lys Glu Arg
         115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                 165                 170                 175

Pro Phe His Phe Tyr Phe Pro Thr Pro Thr Val Leu Cys Asn Glu Ile
                 180                 185                 190

Trp Thr His Ser Tyr Lys Val Ser Asn Tyr Ser Arg Gly Ser Gly Arg
         195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                 245                 250                 255

Ser

<210> SEQ ID NO 11
<211> LENGTH: 214
<212> TYPE: PRT
<213> ORGANISM: Homo sapiens

<400> SEQUENCE: 11

Arg Ile Ala Trp Ala Arg Thr Glu Leu Leu Asn Val Cys Met Asn Ala
 1               5                  10                  15

```
Lys His His Lys Glu Lys Pro Gly Pro Glu Asp Lys Leu His Glu Gln
            20                  25                  30
Cys Arg Pro Trp Arg Lys Asn Ala Cys Cys Ser Thr Asn Thr Ser Gln
            35                  40                  45
Glu Ala His Lys Asp Val Ser Tyr Leu Tyr Arg Phe Asn Trp Asn His
50                  55                  60
Cys Gly Glu Met Ala Pro Ala Cys Lys Arg His Phe Ile Gln Asp Thr
65                  70                  75                  80
Cys Leu Tyr Glu Cys Ser Pro Asn Leu Gly Pro Trp Ile Gln Gln Val
            85                  90                  95
Asp Gln Ser Trp Arg Lys Glu Arg Val Leu Asn Val Pro Leu Cys Lys
            100                 105                 110
Glu Asp Cys Glu Gln Trp Trp Glu Asp Cys Arg Thr Ser Tyr Thr Cys
            115                 120                 125
Lys Ser Asn Trp His Lys Gly Trp Asn Trp Thr Ser Gly Phe Asn Lys
130                 135                 140
Cys Ala Val Gly Ala Ala Cys Gln Pro Phe His Phe Tyr Phe Pro Thr
145                 150                 155                 160
Pro Thr Val Leu Cys Asn Glu Ile Trp Thr His Ser Tyr Lys Val Ser
            165                 170                 175
Asn Tyr Ser Arg Gly Ser Gly Arg Cys Ile Gln Met Trp Phe Asp Pro
            180                 185                 190
Ala Gln Gly Asn Pro Asn Glu Glu Val Ala Arg Phe Tyr Ala Ala Ala
            195                 200                 205
His His His His His His
            210

<210> SEQ ID NO 12
<211> LENGTH: 216
<212> TYPE: PRT
<213> ORGANISM: Homo sapiens

<400> SEQUENCE: 12

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Ser Tyr
            20                  25                  30
Asn Leu Val Ser Trp Tyr Gln Gln His Pro Gly Lys Ala Pro Lys Leu
            35                  40                  45
Met Ile Tyr Glu Gly Ser Lys Arg Pro Ser Gly Val Ser Asn Arg Phe
50                  55                  60
Ser Gly Ser Lys Ser Gly Asn Ala Ala Ser Leu Thr Ile Ser Gly Leu
65                  70                  75                  80
Gln Ala Glu Asp Glu Ala Asp Tyr Tyr Cys Gln Ser Tyr Asp Ser Ser
            85                  90                  95
Leu Ser Val Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
            165                 170                 175
```

-continued

```
Ala Ala Ser Ser Tyr Leu Ser Leu Thr Pro Glu Gln Trp Lys Ser His
        180                 185                 190

Arg Gly Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 13
<211> LENGTH: 6
<212> TYPE: PRT
<213> ORGANISM: Homo sapiens

<400> SEQUENCE: 13

Cys Asp Lys Thr Ser Cys
1               5

<210> SEQ ID NO 14
<211> LENGTH: 7
<212> TYPE: PRT
<213> ORGANISM: Homo sapiens

<400> SEQUENCE: 14

Cys Cys Ser Thr Lys Asp Cys
1               5
```